(12) United States Patent  (10) Patent No.: US 8,795,410 B2
Sato et al.  (45) Date of Patent: Aug. 5, 2014

(54) MONOLITH ADSORBENT AND METHOD AND APPARATUS FOR ADSORBING SAMPLES WITH THE SAME

(75) Inventors: Atsushi Sato, Fukushima (JP); Hiroyuki Terashima, Fukushima (JP); Yoshiyuki Takei, Saitama (JP)

(73) Assignee: GL Sciences Incorporated (JP)

( * ) Notice: Subject to any disclaimer, the term of this patent is extended or adjusted under 35 U.S.C. 154(b) by 234 days.

(21) Appl. No.: 12/665,612

(22) PCT Filed: Jun. 18, 2008

(86) PCT No.: PCT/JP2008/061507
§ 371 (c)(1),
(2), (4) Date: Jan. 5, 2010

(87) PCT Pub. No.: WO2008/156199
PCT Pub. Date: Dec. 24, 2008

(65) Prior Publication Data
US 2011/0023711 A1  Feb. 3, 2011

(30) Foreign Application Priority Data
Jun. 18, 2007 (JP) ................. 2007-160803

(51) Int. Cl.
*G01N 30/52* (2006.01)
*B01J 20/281* (2006.01)
*B01J 20/28* (2006.01)
*B01J 20/286* (2006.01)
*B01J 20/32* (2006.01)

(52) U.S. Cl.
CPC .......... *B01J 20/28042* (2013.01); *B01J 20/281* (2013.01); *B01J 20/286* (2013.01); *B01J 20/3204* (2013.01); *B01J 2220/54* (2013.01); *G01N 30/52* (2013.01); *G01N 2030/528* (2013.01)
USPC ...... 95/88; 96/101; 96/154; 96/413; 502/400; 210/660

(58) Field of Classification Search
CPC ............ B01J 20/08; B01J 20/14; B01J 20/18; B01J 20/20; B01J 20/205; B01J 20/28042; B01J 20/281; B01J 20/286; B01J 20/3204; B01J 20/321; B01J 2220/54; B01J 2220/82; B01J 2220/825; G01N 2030/528; G01N 30/52
USPC .............. 95/85, 88, 90, 107, 903; 96/96, 101, 96/108, 150, 153, 154, 413; 502/400–402, 502/410, 412, 415, 416; 210/660, 502.1; 73/23.35
See application file for complete search history.

(56) References Cited

U.S. PATENT DOCUMENTS 4,386,947 A * 6/1983 Mizuno et al. .................. 96/137
4,800,190 A * 1/1989 Smolik .......................... 502/416
(Continued)

FOREIGN PATENT DOCUMENTS

EP 1758945 12/2005
JP 2002301367 10/2002
(Continued)

OTHER PUBLICATIONS

International Search Report and Written Opinion based on PCT/JP2008/061507 dated Jan. 7, 2010.
(Continued)

*Primary Examiner* — Frank Lawrence
(74) *Attorney, Agent, or Firm* — Hahn Loeser & Parks LLP

(57) ABSTRACT

The problem to be solved by the present invention is to provide a monolith adsorbent which can adsorb a target sample easily in a short time or regardless of whether the amount of the sample is small or large and extract the sample with a small amount of solvent, and easily secure the sample necessary for analysis, and a method and an apparatus for adsorption and retention using the same. The present invention is a monolith adsorbent formed by allowing a monolith structure body to contain an adsorbing material such as activated carbon or graphite, exposing the adsorbing material on the surface of the structure body and further surface-treating the surface of the monolith structure body with a hydrophobic or hydrophilic compound or a resin.

33 Claims, 41 Drawing Sheets

(56) References Cited

U.S. PATENT DOCUMENTS

| | | | |
|---|---|---|---|
| 4,992,084 A * | 2/1991 | Von Blucher et al. | 96/131 |
| 5,288,306 A * | 2/1994 | Aibe et al. | 95/141 |
| 5,308,457 A * | 5/1994 | Dalla Betta et al. | 95/143 |
| 5,704,967 A * | 1/1998 | Tom et al. | 96/143 |
| 5,750,026 A * | 5/1998 | Gadkaree et al. | 210/502.1 |
| 6,764,755 B2 * | 7/2004 | Tom et al. | 428/304.4 |
| 6,860,924 B2 * | 3/2005 | Rajagopalan et al. | 96/154 |
| 7,456,131 B2 * | 11/2008 | Klett et al. | 502/417 |
| 7,595,350 B2 * | 9/2009 | Xu | 516/111 |
| 8,404,346 B2 * | 3/2013 | Walter et al. | 428/405 |
| 2007/0215547 A1 * | 9/2007 | O'Gara | 210/656 |
| 2007/0227351 A1 * | 10/2007 | Garcia-Martinez | 95/90 |
| 2008/0032116 A1 | 2/2008 | Hosoya et al. | |

FOREIGN PATENT DOCUMENTS

| | | |
|---|---|---|
| JP | 2006015333 | 1/2006 |
| JP | 2007145636 | 6/2007 |
| WO | 9503256 | 2/1995 |
| WO | 2005116095 | 12/2005 |
| WO | 2007021037 | 2/2007 |

OTHER PUBLICATIONS

Yu, J et al., Hydroxyfullerene as a novel coating for solid-phase microextraction fiber with sol-gel technology, Journal of Chromatography, 2002, pp. 37-48, vol. 978, Elsevier Science Publishers B.V., China.

Nakanishi, K., Pore Structure Control of Silica Gels Based on Phase Seperation, Journal of Porous Materials, 1997, pp. 67-112, vol. 4, Kluwer Academic Publishers. Manufacturered in The Netherlands, Japan.

Supplementary European Search Report and Search Opinion dated Mar. 22, 2011 of EP Application No. EP 08 76 5828 based on PCT/JP2008/061507.

* cited by examiner

MONOLITH ADSORBENT AND METHOD AND APPARATUS FOR ADSORBING SAMPLES WITH THE SAME

TECHNICAL FIELD

The present invention relates to a monolith adsorbent and a method and an apparatus for adsorbing a sample with the same.

BACKGROUND ART

Solid-phase micro extraction (SPME) method and stir bar sorption extraction (SBSE) method have been suggested as sample extracting method for introducing a sample to an analyzer (GC, LC, etc.).

The both methods are sample extracting methods applying the principle of solvent extraction which use a liquid phase as a stationary phase and transfer of substance in accordance with partition coefficient. Therefore, when a rapid sample extraction at a high recovery ratio is to be performed, there are involved various factors such as kind and film thickness of the stationary phase, extraction temperature, salting-out, extraction time, sample amount, pH adjustment, influences by contaminating substances and stirring rate and these methods are disadvantageous in the practical use.

SPME is a concentration method which aims at allowing a liquid phase such as PDMS coated on a glass fiber, glass, etc. or an adsorbing material mixed with the liquid phase to retain solute components dissolved in a solution in accordance with phase equilibrium as disclosed in Japanese Patent No. 3081239.

In this method, the thus held solute components can be inserted into the injection port of GC just as they are and vaporized and desorbed inside the injection port of GC.

In the meantime, SBSE includes a method using a magnet-embedded glass piece coated with a liquid phase such as PDMS, which is put in a vial bottle. The glass piece has the function of performing stirring in the target sample as disclosed in Japanese Patent No. 3462443.

The methods mentioned above have spread as methods which enable to perform concentration analysis very inexpensively and readily, and as simple and convenient apparatus for concentration analysis of samples such as food, fragrance components, clean water VOC, atmosphere and pesticides.

The retention ratio of the sample in the solution by the SPME currently performed in accordance with phase equilibrium is generally from several % to around 30%. In order to improve the extraction of the substance in the sample solution (i.e., for increasing the partition coefficient) in SPME and SBSE, it is necessary to increase the adsorbed sample amount by increasing the volume of the stationary phase.

However, increase in the volume of the stationary phase leads to the increase in the thickness thereof, and as a result, it takes an extended time to reach the condition where the concentration of stationary phase and the concentration in the sample solution are in the equilibrium.

It also takes time to extract (desorb) the adsorbed target substance from the sample solution with heat or a solvent, and the peak of the chromatogram becomes broad.

Furthermore, there is a defective that the heat for an extended time causes decomposition of a target component. In addition, when the adsorbed amount of a target component is small, equilibrium collapses due to the existence of the matrix, which makes difficult to allow correct adsorption.

In addition, PDMS is applied only to the surface of the glass fiber or the glass and has small surface area. Therefore the amount of the liquid phase which can be held is restrictive, and the absolute recovery ratio is low.

On this account, an object of the present invention is to provide a monolith adsorbent which can adsorb a sample solution of an extremely small amount or in a low concentration readily in a short time, enables to extract the components held thereby with a small amount of solvent or heating for a short time, and enables to secure the sample necessary for the analysis extremely easily as well as an adsorption method and an apparatus using the same.

Another object of the present invention is to provide a monolith adsorbent material with better adsorption efficiency for thermal desorption and with better solvent extraction efficiency than those used in the conventional solid-phase extraction methods, and it enables downsizing.

DISCLOSURE OF THE INVENTION

The present invention, as means for solving the problems mentioned above, is directed to a monolith adsorbent characterized in that the monolith adsorbent has an adsorbing material contained in a monolith structure body and exposed on the surface of the structure body and a chemical substance is applied or chemically bonded to the structure body.

The present invention is also directed to a monolith adsorbent characterized in that the adsorbing material is one or a mixture of plural kinds of materials selected from activated carbon, graphite carbon, carbon nanotube, fullerene, molecular sieve, zeolite, diatomaceous earth, divinylbenzene copolymer, molecular sieve carbon, activated alumina and Florisil.

The present invention is also directed to a monolith adsorbent characterized in that a chemical substance having hydrophobicity or hydrophilicity is chemically bonded to the surface of the monolith structure body.

The present invention is also directed to a monolith adsorbent characterized in that a resin is applied or chemically bonded to the surface of the monolith structure body.

The present invention is also directed to a monolith adsorbent characterized in that a resin is further applied or chemically bonded to the monolith structure body which has been surface-treated with the chemical substance having hydrophobicity or hydrophilicity.

The present invention is also directed to a monolith adsorbent characterized in that the chemical substance having hydrophobicity comprises one or more kinds of compounds having a functional group selected from an octadecyl group, a methyl group, an ethyl group, an octyl group and a cyclohexyl group, a vinyl group, and a phenyl group.

The present invention is also directed to a monolith adsorbent characterized in that the chemical substance having hydrophilicity is one or more kinds of compounds having a functional group selected from a diol group, a cyanopropyl group, a carboxethyl group, a propylsulfonyl group, a benzenesulfonylpropyl group, an aminopropyl group, an ethylenediamine N-propyl group, a trimethylaminopropyl group, and a polyamide group.

The present invention is also directed to a monolith adsorbent characterized in that the resin comprises one or a mixture of plural kinds of compounds selected from resins having a siloxane backbone, resins having hydrophilicity and resins having hydrophobicity.

The present invention is also directed to a monolith adsorbent characterized in that the resin having a siloxane backbone comprises one or a mixture of plural kinds of compounds selected from polydimethylsiloxane, silphenylene siloxane, diphenylsiloxane, cyanopropylphenylsiloxane and cyanopropylsiloxane.

The present invention is also directed to a monolith adsorbent characterized in that the resin having hydrophilicity comprises one or a mixture of plural kinds of compounds selected from polyethylene glycol, polyethylene glycol terephthalate, polypropylene, glycol, carbowax, polyacrylic acid and polyamine.

The present invention is also directed to a monolith adsorbent characterized in that the resin having hydrophobicity comprises one or a mixture of plural kinds of compounds selected from divinylbenzene copolymers, styrene copolymers and propylene copolymers.

The present invention is also directed to a method for adsorbing a sample characterized in that the method comprises containing a monolith adsorbent in a container accommodating a liquid or gaseous sample and impregnating the monolith adsorbent in the sample wherein the monolith adsorbent is constructed by containing an adsorbing material in a monolith structure body while exposing the adsorbing material on the surface of the structure body and surface-treating the structure body.

The present invention is also directed to a method for adsorbing a sample characterized in that the method comprises containing a monolith adsorbent in a container accommodating a liquid or a gaseous sample and stirring in the sample wherein the monolith adsorbent is constructed by containing an adsorbing material in a monolith structure body while exposing the adsorbing material on the surface of the structure body and surface-treating the structure body.

The present invention is also directed to a method for adsorbing a sample characterized in that the method comprises containing a monolith adsorbent in a container accommodating a gaseous sample and performing passive sampling wherein the monolith adsorbent is constructed by containing an adsorbing material in a monolith structure body while exposing the adsorbing material on the surface of the structure body and surface-treating the structure body.

The present invention is also directed to a method for adsorbing a sample characterized in that the method comprises inserting a tube accommodating a monolith adsorbent into a gas phase part of a vial, blowing an inert gas such as He and $N_2$ into the sample from outside of the vial through a vial cap to transfer a target component in the sample to the gas phase part of the vial and to allow the monolith adsorbent to retain the same wherein the monolith adsorbent is constructed by containing an adsorbing material in a monolith structure body while exposing the adsorbing material on the surface of the structure body and surface-treating the structure body.

The present invention is also directed to an apparatus for adsorbing a sample characterized in that the apparatus comprises a filter having a monolith structure body and a monolith adsorbent for allowing a target component in the sample which has passed through the filter to be adsorbed thereby in a container accommodating a liquid or gaseous sample or in a flow channel wherein the monolith adsorbent is constructed by containing an adsorbing material in a monolith structure body while exposing the adsorbing material on the surface of the structure body and surface-treating the structure body.

The present invention is also directed to an apparatus for adsorbing a sample characterized in that the filter is formed in the form of a container and the monolith adsorbent is provided in the container for adsorbing a target component.

The present invention is also directed to an apparatus for adsorbing a sample characterized in that the monolith structure body in the filter has a through-pore which is formed larger than the through-pore of the monolith adsorbent.

The present invention is also directed to an apparatus for adsorbing a sample characterized in that the monolith structure body in the filter has been reacted with a hydrophilic or hydrophobic compound or an ionic functional group.

The present invention is also directed to an apparatus for adsorbing a sample characterized in that a monolith structure body is disposed on a rotating stirrer to allow the monolith adsorbent to adsorb a target component by rotating the stirrer wherein the monolith adsorbent is constructed by containing an adsorbing material in a monolith structure body while exposing the adsorbing material on the surface of the structure body and surface-treating the structure body.

The present invention is also directed to an apparatus for adsorbing a sample characterized in that a monolith adsorbent is attached in a closely contactable container to increase the sample contact efficiency in adsorbing and extracting a target component from a liquid or gaseous sample wherein the monolith adsorbent is constructed by containing an adsorbing material in a monolith structure body while exposing the adsorbing material on the surface of the structure body and surface-treating the structure body.

Although the present invention uses a stationary phase having the same volume as in SPME and SBSE, the thickness of the stationary phase itself is reduced while the surface area is increased by using a monolith structure body, and as a result, adsorbing (to reach the equilibrium) and extracting (desorbing) the component can be performed in a short time.

In addition, the effect by the adsorbing material exposed on the surface of the monolith structure body and the effect by the hydrophobic or hydrophilic compound such as octadecylsilane (ODS) and styrene divinylbenzene copolymer (SDB) or diols which have been reacted with the surface of the monolith structure body are synergistic and thus the adsorption ability can be optionally enhanced by further performing surface treatment by applying a resin (polydimethylsiloxane (PDMS), polyethylene glycol (PEG), etc.) to the whole monolith adsorbent.

Besides, the monolith structure body has continuous pore structures and a number of mesopores and therefore has a large surface area. Accordingly, the contact area of the sample components in the target solution and the adsorbing material and the alkoxysilane based samples such as ODS is large, which enhances the adsorption ability.

The synergistic effects of the surface area, adsorbing materials, hydrophobic or hydrophilic compounds, reagents and so on as mentioned above enable to improve the adsorption of the sample.

When a sample compound retained by PDMS or the like is eluted, release proceeds in accordance with phase equilibrium and therefore the conventional methods with a small surface area are disadvantageous. In contrast, since the present method uses a monolith adsorbent having a large surface area, the contact area with a gas or a solvent for desorption at the time of elution is large and release of an extremely small amount of gas or a solute component in the solvent is enabled.

In addition, increase in the surface area and improvement in the ability of adsorption mean the downsizing of monolith adsorbents in itself and have significance particularly in GC and LC analysis. For example, if the adsorbent of the present invention can be accommodated in a current GC auto-sampler vial, desorption of the components can be performed with a small amount of a solvent, and an autoanalysis with the auto-sampler is enabled in a state as it is, and thus concentration and analysis is enabled extremely readily and inexpensively.

When environmental water is concentrated and analyzed, there is a case that a matrix component coexisting in the environmental water may interfere with the analysis of the target sample. Currently, the interfering components are removed by pre-filtration and the like before concentration, this step is often time-consuming and troublesome.

In contrast, the method of the present invention enables the removal of the interfering components and selective adsorption and retention of the target sample alone at a time. The matrix is removed by a monolith structure body of the covering part and further the target sample alone is selectively adsorbed in the inner adsorption monolith material.

In addition, the same effect can be obtained when a disk-shaped matrix removal mechanism 50 (which corresponds to the above-mentioned covering part) is provided in the container so that monolith adsorbents 51 may be in a close contact with the container (FIG. 29).

Further effect in the aspect of adsorbed amount, adsorption time and readiness in adsorption (several times of pumping) can be obtained by precisely sending the sample solution to the matter monolith adsorbent of the present invention. Recovering effect with a little solvent results by sending the solvent for extraction of a target component in the same way, and as a result, analysis in high concentration is enabled.

In addition, an effect of reducing the desorption time is resulted in the thermal desorption. These effects result in sharp peaks in the chromatogram and suppresses thermal decomposition of the target components, and also lead to the effect that sufficient adsorbed amount can be obtained without being affected by the existence of the matrix.

In addition, according to the monolith adsorbent of the present invention, the sample which has been adsorbed in the monolith adsorbent can be extracted by a solvent or heat and can be introduced into the analyzer just as it is. That is, the laborious steps of eluting the sample in a container and then transferring the sample to the injection port as performed in the conventional method can be omitted, and that the present method has effects that the desorption is possible with only a little solvent and the thermal desorption can be facilitated.

The sample can be surely held in the apparatus and method of the present invention when a large amount of the sample in a low concentration is made to flow without outflow (breakthrough, etc.) of the target sample from the adsorbing material. The structure body can surely retain the sample with least possibility of being damaged.

In the present invention, the sample as either a liquid or a gas can be handled, and a liquid sample can be applied to pumping, impregnation, stirring in the solution, headspace, dynamic headspace, a stirrer or the like and a gaseous sample can be applied both to an active sampler and a passive sampler.

BEST MODE FOR CARRYING OUT THE INVENTION

The present invention will be described below in detail. As the surface area and through-pore size when used as monolith adsorbent, the following values are generally used.

Preferably, the surface area is from 100 $m^2/g$ to ideally 1,000 $m^2/g$ (actually, up to around 350 $m^2/g$), the through-pore is from 1 μm to 100 μm, and when used as a pre-filter the surface area is 10 $m^2/g$ or less, and the through-pore is from 1 μm to 100 μm.

The present invention is preferably carried out under the following conditions but not limited thereto.

Figure 2:
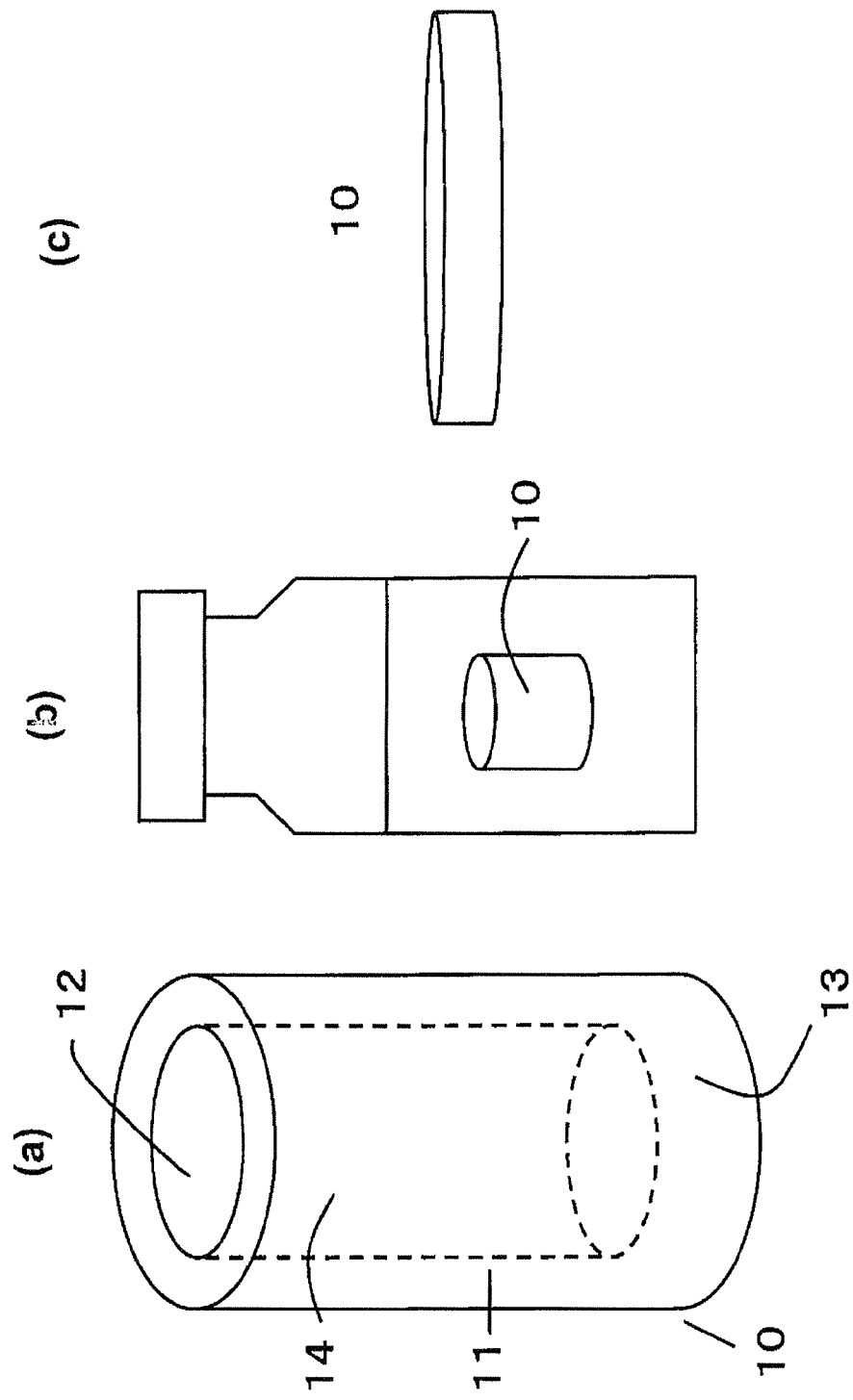
FIG. 2 is a perspective view of an example of the present invention.

Activated carbon:
Particle diameter: 3 to 10 μm
Surface area: 800 $m^2/g$
Pore volume=0.500 cc/g
Pore diameter: 24.00 angstroms
Monolith structure body:
Through-pore size: 5 to 15 μm
Monolith adsorbent:
Adsorbing material content: 1.5 to 3%
Surface area: 600 to 700 $m^2$ The monolith adsorbent 10 forms an elongated cylindrical body 11 consisting of a porous body which is a single structure body having continuous through-holes in the form of a three-dimensional network known as so-called a monolith structure body, and as the monolith adsorbent, a cylindrical body (a) having an opening 12 at the upper end and a bottom 13 at the lower end to form a accommodation part 14 is conceivable. In addition to this, forms like a disk and semi-cylindrical body and so on can be selected depending on the shape of the insert described later. (FIG. 2)

The monolith structure body is preferably one having pores and regularly forming a continuous network structure but not limited to this.

Furthermore, the shape having a through-hole in the center to fix the monolith adsorbents at the time of adsorption is also conceivable. A stick consisting of a metal or a resin and having edge faces subjected to a bending process or a pipe having a large diameter can be inserted into the through-hole to fix it.

The porous body used in the present invention has pores as described below and the pores have a structure which continuously communicates the upper end and the lower end, i.e., so-called monolith structure. Besides, the pore in the axial section is preferably a circle or a form close to a circle and the materials of the porous body is not particularly limited but, for example, a porous body of an inorganic material such as porous ceramic and porous glass, for example, porous glass is desirable. Examples of the porous ceramic include compounds of 4 group elements such as silica and titanium, zirconium and hafnium, those based on alumina silicate A (sintered hard porcelain particles), silica sand, alumina, alumina silicate B (sintered chamotte particles), porous mullite or diatomaceous earth.

Examples of the porous glass include those having a composition based on $NaO-B_2O_3-SiO_2-CaO$, and may be produced from glasses to which various kinds of oxides such as $Al_2O_3$, $ZrO_2$, $ZnO_2$, $TiO_2$, $SnO_2$, $MgO_2$ are added. A method of preparing by forming an interlocking separate phase structure utilizing a separate phase phenomenon of borosilicate glass caused by heat treatment and then eluting one phase with an acid has been proposed. For example, silica sand, boric acid, soda ash and alumina are mixed and molten at 1200 to 1400° C. This is molded at 800 to 1100° C. to form an unseparated phase borosilicate glass and after phase separated by heat treatment into a $SiO_2$ phase and a $B_2O_3-Na_2O-CaO$ phase, acid treatment is performed to leave a porous body having a $SiO_2$ skeleton. Those having pores with a uniform diameter distribution ranging from 0.1 to 10 micron can be produced by changing the condition at the time of the heat treatment in accordance with the use. The porous ceramics are produced by mixing, molding and sintering, for example, ceramics particles (including hard porcelain particles, silica, alumina, chamotte) of the particle diameter in a certain range and the pore formation materials, for example, crystal cellulose (Asahi Chemical Industry:Apicel) and suitable dispersion solvent. Those having pores with a uniform diameter distribution ranging from about 500μ to 0.1μ or more can be produced in accordance with the use.

The surface of the pores mentioned above can be modified or treated by applying a coating agent and/or a chemical modifier suitable for sample separation used for conventional fillers. Examples of the coating agent include polyethylene glycol and silicone oil. Examples of the chemical modifier include various silane treatment agents such as alkylchlorosilanes such as trimethylchlorosilane (TMS), dimethyl-n-octylchlorosilane, dimethyl-n-octadecyl chlorosilane (ODS), aminoalkoxysilanes such as γ-aminopropyltriethoxysilane and other silane treatment agents such as epoxysilanes. Furthermore, polymer compounds such as proteins or low molecular weight compounds may be linked to the modifier group of the surface modifier.

In addition to the porous bodies mentioned above, use of a porous body having a structure filled with porous bodies mentioned above having micropores in the pores thereof is recommended. This is further explained.

The macropores of a skeleton having macropores are impregnated with a monomer to form micro porous bodies. The monomer is polymerized in the macropores utilizing a solvent which is added beforehand to thereby for a porous body having a structure filled and integrated with porous bodies having micropores which are smaller than macropores and have an open structure. In this case, the monomer to form micro porous bodies may be either organic or inorganic material, and in the case of the inorganic system, a catalyst such as hydrochloric acid is added to tetraethoxysilane to prepare and impregnate the sol, and a porous silica glass which has micropores can be formed after aged.

In the case of the organic system, various resins can be selected and, for example, a polyacrylamide gel porous body can be obtained by impregnation with acrylic amide monomers followed by polymerization. It is desirable to use heat-resistant resins because the above-mentioned resins do not have anti-heat performance so that they can endure heating. The range of these micropores is decided depending on the molecular size of the target component to be separated in the liquid. Chemical substances can sufficiently enter the inside of the pores by liquid affinity if the is 1,000 nm at the largest, even if they have higher-order structures in a liquid such as proteins. Preferably the range is 100 to 500 nm.

In the meantime, there is known a method for preparing inorganic porous bodies by sol-gel method which proceeds as a liquid-phase reaction. In the sol-gel method, so-called polymerizable low molecular weight compounds are generated to ultimately obtain aggregates and polymers, and the following methods are used.

Specifically it is a method comprising dissolving a water-soluble polymer and nonionic surfactant in an acidic aqueous solution, adding a metal compound having a hydrolysable functional group thereto to perform a hydrolysis reaction, allowing the product to be solidified and subsequently performing dry heating or solvent substitution. This method utilizes a phenomenon that the water-soluble polymer and the nonionic surfactant which has dissolved uniformly causes phase separation in the process of hydrolysis/polymerization of metalalkoxides or oligomers.

A nonionic surfactant and a thermally-degradable property compound are dissolved in an acidic aqueous solution, a metal compound having a hydrolysable functional group is added thereto to perform a hydrolysis reaction allowing the product to be solidified, and then the gel in a wet condition is heated to heat decompose the low molecular weight compound dissolved beforehand at the time of adjusting the gel and the product is dried and heated. Here, the metalalkoxides or the oligomers are preferably those having a small number of carbon atoms such as a methoxy group, an ethoxy group and a propoxy group.

Si, Ti, Zr or Al1 are used, for example, for the metal, which are metals of the oxides finally formed. The metals may be one single metal or two or more kinds of metals. Silicon alkoxides are preferable and, as silicon alkoxides, can be used tetramethoxysilane, tetraethoxysilane, methyltrimethoxysilane, ethyltrimethoxysilane, vinyltrimethoxysilane but not particularly to these.

On the other hand, oligomers may be those which can be uniformly dispersed in the alcohol and specifically oligomers up to decamer can be used. The organic polymers are preferably mixed in the ratio of 0.03 to 0.40 part by weight for 1 oligomeric part by weight of the metalalkoxide or oligomer thereof.

The water-soluble organic polymers are those which cause phase separation in a process of hydrolysis and uniformly dissolve in the alkoxide generated by the hydrolysis of the metalalkoxide or the oligomer thereof, or the alcohol containing liquid generated by the hydrolysis of the oligomer thereof. Specifically, sodium salts of polystyrene sulfonic acid which are polymer metal salts, polyallylic acids or the like which are polymer acids and dissociated to form polyanions, polyallylamines and polyethyleneimines or the like which are polymer bases and form polycations in aqueous solutions or polyethylene oxides or the like which are neutral polymers and have ether bonds in the main chain and polyvinylpyrrolidone or the like having v-lactam in the side chains are preferable.

The nonionic surfactant is a material having functions of inducing the sol-gel transition and the phase separation process at the same time and thereby gelating and separating into a solvent-rich phase and a skeleton phase at the same time.

The nonionic surfactants are those having a hydrophilic moiety such as polyoxyethylene and a hydrophobic moiety mainly consisting of alkyl groups and, for example, polyoxyethylene nonyl phenyl ether, polyoxyethylene octyl phenyl ether, polyoxyethylene alkyl ether and those containing polyoxypropylene as a hydrophilic moiety, for example, polyoxypropylene alkylether is preferable but not be limited to these. The amount of the nonionic surfactant to add changes depending on the kind of the surfactant, the kind and the amount of the metalalkoxide but it is 1.0 to 10.0 g, preferably 1.5 to 6.0 g for 10 g of the metalalkoxide.

When a nonionic surfactant and a thermally-degradable compound are dissolved in an acid aqueous solution and a metal compound having a hydrolysable functional group is added thereto to perform a hydrolysis reaction, a gel which is separated into a solvent-rich phase and a skeleton phase are formed. After the product (gel) is solidified, it is aged for an appropriate time and then the wet gel is heated. Thereby the thermally-degradable compound which has been dissolved in the reaction solution beforehand is heat decomposed and the pH of a solvent in contact with the inner wall surface of the skeleton phase increases.

And the solvent erodes the inner wall surface and changes the convexo-concave state of the inner wall surface to extend pore diameters slowly. As the acidic aqueous solution used at this time, mineral acids, typically hydrochloric acid, nitric acid or the like having 0.001 N or more are preferable. The solution is put in an airtight container and held at temperature 40 to 80° C. for 0.5-5 hours and thereby achieving the hydrolysis. The hydrolysis proceeds as the transparent solution at first becomes cloudy and phase separation from the organic polymer occurs and finally reaches gelation. The organic polymer or the polymer thereof is in a dispersion state during this hydrolysis process, and precipitation thereof is not caused substantially. The thus generated gel is left untouched at 40 to 80° C. for several hours to around dozens of hours for aging and then washed with water to remove the organic polymer and sintered at around 800 to 1000° C. to obtain porous glass.

The adsorbing materials to be contained in the monolith adsorbent in itself include activated carbon, graphite carbon, carbon nanotube, fullerene, molecular sieve, silica gel, zeolite, diatomaceous earth, devinylbenzene copolymers (styrene divinylbenzene, etc.), molecular sieve carbon, activated alumina and Florisil (magnesium silicate). One or several kinds of these adsorbing materials are mixed and added to a sol-gel solution and uniformly dispersed therein.

Production Method (Addition of Adsorbing Material)

An appropriate amount (0.1 to 20%) of an adsorbing material (activated carbon, molecular sieve, resin type adsorbing materials such as styrene divinylbenzene, graphite, zeolite, diatomaceous earth, etc.) is added to a sol-gel solution and the solution is stirred with a stirring bar or a supersonic wave washer and an appropriate amount of the solution is rapidly drained into a mold. Here, it is one of the factors which increase adsorption ability to crush the adsorbing materials mentioned above and minimize the particle diameter before adding them to the above solution. It is desirable to make the average diameter to less than 5 μm. When crushed finely, the activated carbon or the like can be mixed with hard small particles such as molecular or silica and subjected to crushing, and thereby finer particles can be obtained.

The molecular sieve or silica mentioned above do not have to be removed later, and to the contrary, they can be mixed with the adsorbing materials, which can increase the adsorption ability.

(Gelation and Hardening Process)

The sol-gel solution is filled in a mold and sealed up and gelated in a constant-temperature bath at an appropriate temperature (for one hour to one day or more). Then, the monolith structure body taken out of the mold is neutralized with pure water and dipped in an alkali aqueous solution (in the case for increasing mesopores) or pure water (when mesopores are not required) and heated to promote hardening.

(Sintering Process)

After the processing mentioned above is finished, the monolith structure body is neutralized (with pure water) and dehydrated and dried. Then, the monolith structure body is put in a metal tube and inert gas (He, $N_2$) is flowed from the one side.

(Exposing Process of Adsorbing Material)

After sintered, the monolith structure body is dipped in an alkali aqueous solution (for example, sodium hydroxide, potassium hydroxide, ammonium solution) of a suitable concentration to expose much adsorbing material on the surface and subjected to heat treatment (40 to 200° C.). Then, it is neutralized (with pure water) and dried.

In addition to the method mentioned above, the surface thereof may be polished with a file.

(Surface Treatment of Surface of Monolith Structure Body)

As the method for chemical treatment of the monolith structure body, methods for providing hydrophilicity or hydrophobicity are recommended.

As the method for providing hydrophobicity, the monolith structure body after dried is subjected to acid treatment, neutralized (with pure water), dried and impregnated with a reactive reagent such as alkoxysilane and chlorosilane having a group such as an octadecyl group, a methyl group, an ethyl group, an octyl group, a cyclohexyl group, a vinyl group and a phenyl group and reacted by heat. Respective functional groups may be either a mono, di or tri group.

For example, the methyl group may be a dimethyl group, a trimethyl group or a tetramethyl group as well. After the reaction, the monolith structure body is washed with an organic solvent, dried and heated while inert gas is flowed therethrough.

Furthermore, secondary hydrophobing is recommended to enhance hydrophobicity. Non-activity is enhanced by performing this secondary processing and enables to reduce surface adsorption. When the hydrophobic compound mentioned above has long side chains such as an octadecyl group and an octyl group, in the secondary processing, the surface may not be perfectly modified, and therefore, it is preferable perform modification again.

In that case, the monolith structure body is impregnated with an alkoxysilane reagent containing short side-chains such as a methyl group, an ethyl group, a phenyl group, and a vinyl group and reacted by heat. After the reaction, the monolith structure body is washed with an organic solvent, dried and heated while inert gas is flowed therethrough.

As this processing is further repeated, hydrophobicity can be adjusted but the effect saturates in the processing at or after the third time, twice treatment is recommended.

The hydrophobing treatment mentioned above enables to the monolith structure body to be floated on the water, and thus it becomes suitable for adsorbing components present only in a small amount in the water, selectively adsorbing a hydrophobic compound and providing high inertness. The hydrophobing treatment can be adjusted by changing the kind of the binding groups and the times of treatment and so treatment in accordance with the purpose can be enabled.

(Surface Treatment of Surface of Monolith Structure Body)

As the method for providing hydrophilicity, the monolith structure body after dried is subjected to acid treatment, neutralized (with pure water), dried and impregnated with a reactive reagent having hydrophilicity such as those having a group such as a diol group, a cyanopropyl group, a carboxethyl group, a propylsulfonyl group, a benzenesulfonylpropyl group, an aminopropyl group, an ethylenediamine N-propyl group, a trimethylaminopropyl group, a polyamide group and reacted by heat. After the reaction, the monolith structure body is washed with an organic solvent, dried and heated while inert gas is flowed therethrough.

By performing hydrophilizing treatment mentioned above, it becomes suitable for adsorbing a hydrophilic compound present only in a small amount in non-aqueous solvent such as oil, gasoline and hexane and selectively adsorbing a hydrophilic compound.

(Applying/Chemical Bonding Resin on Surface of Monolith Structure Body)

Furthermore, it is recommended to further apply a resin or perform a chemical treatment on the surface of the monolith structure body which has been subjected to a hydrophobing or hydrophilizing treatment.

Examples of the resin include one or a mixture of plural kinds selected from polydimethylsiloxane, silphenylene siloxane, diphenylsiloxane, cyanopropylphenylsiloxane, cyanopropylsiloxane as resins having a siloxane skeleton.

Examples of the resin having hydrophilicity include one or a mixture of plural kinds selected from polyethylene glycol, polyethylene glycol terephthalate, polypropylene, glycol, carbowax, polyacrylic acid and polyamine, and examples of the resin having hydrophobicity include one or a mixture of plural kinds selected from divinylbenzene copolymers, styrene copolymers and propylene copolymers.

The monolith structure body is impregnated in a solution in which the resin mentioned above is diluted in an appropriate concentration by a solvent and performing coating or chemical bonding by removing the solvent or a heat reaction. Thereby applying or chemical bonding a resin on the monolith structure body can be performed.

The amount of chemical substances on the surface of the monolith structure body is increased by applying or chemical bonding a resin and, as a result, the target component can be loaded in more amount.

Actually, adsorption of the target component is enabled by directly applying or chemical bonding a resin on the surface of the monolith structure body.

However, treatment with a resin after the treatment with a chemical substance having hydrophilicity or hydrophobicity as described above is recommended in the selective adsorption from the matrix containing sample.

Mold

Figure 3:
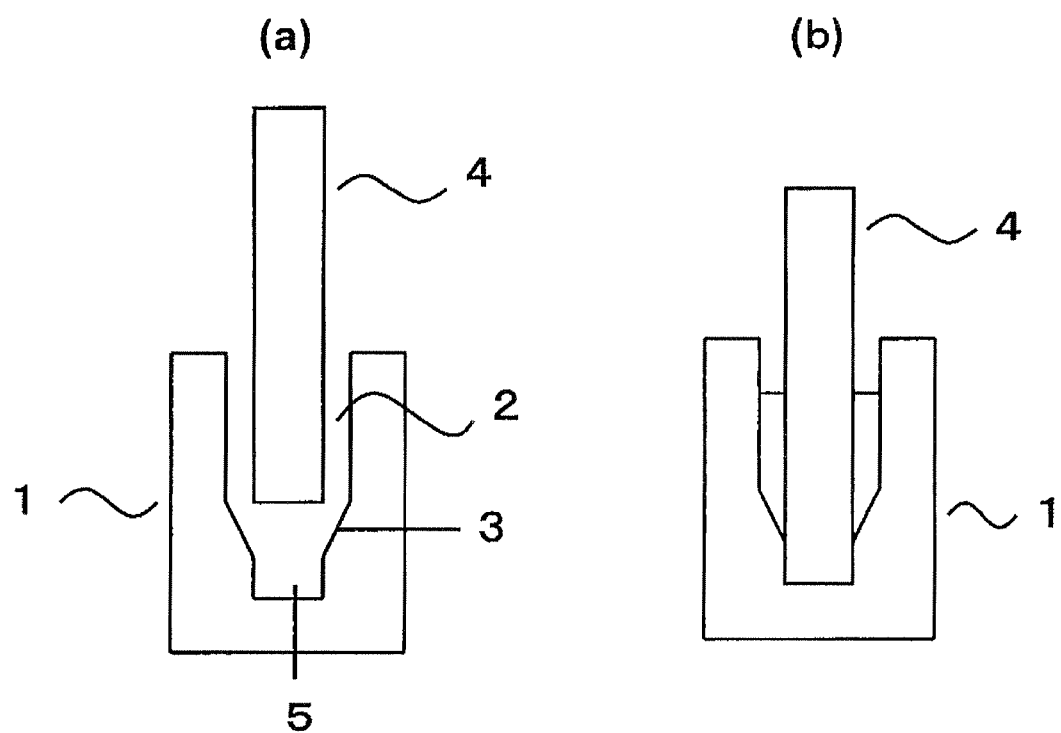
FIG. 3 is a schematic view illustrating the preparation in an example of the present invention.
Figure 4:
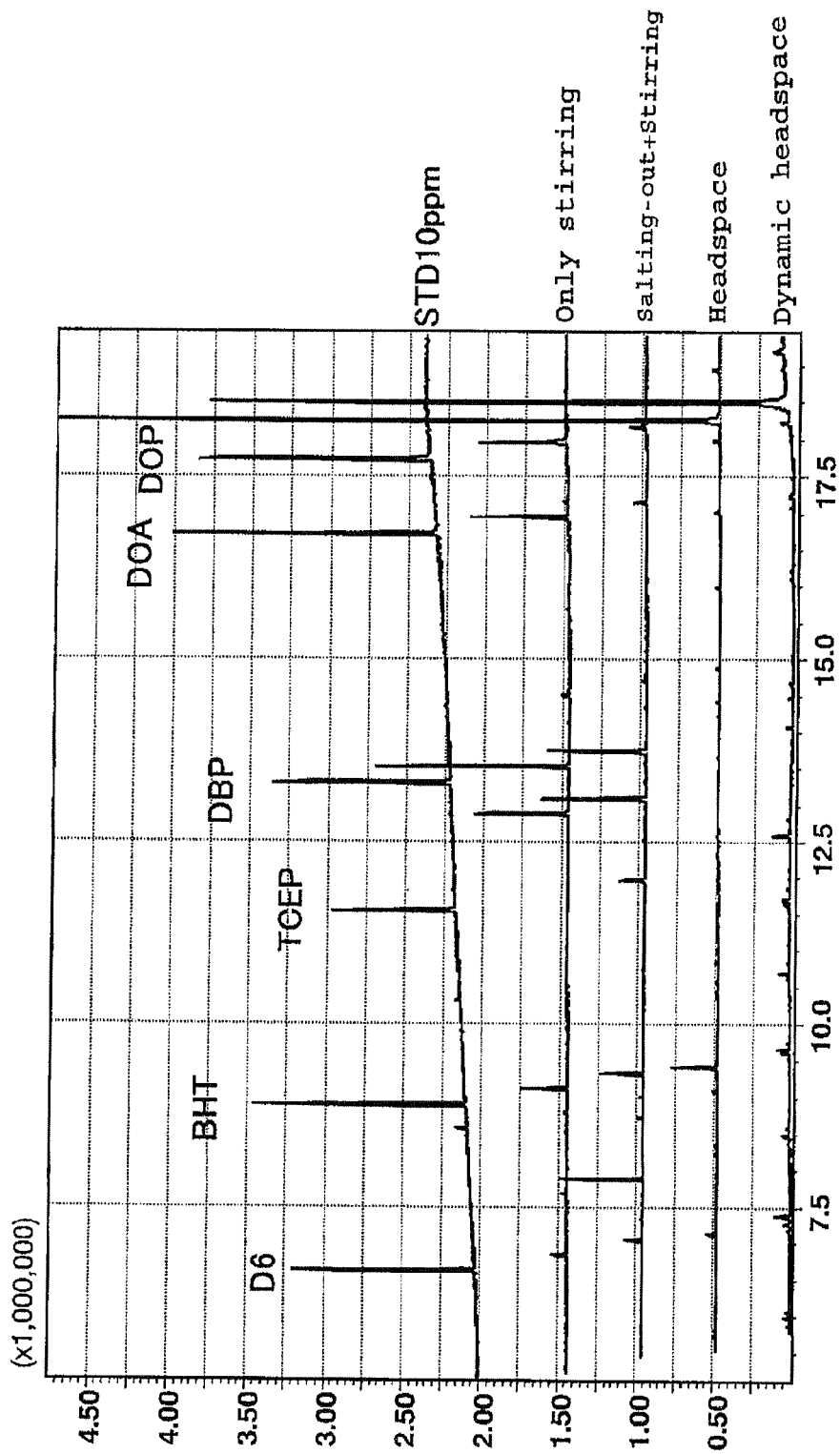
FIG. 4 is a chromatogram analyzing a plasticizer in an example of the present invention.

The monolith structure body is prepared using a mold as shown in FIG. 3.

A hydrophilic resin material 1 (PEEK material, etc.) is used for the base material of the mold and an opening 2 which does not penetrate the mold is provided in the resin material 1. The end part is formed in the shape of a cone shape 3 so that the shape may match the shape of the GC auto-sampler vial. A resin stick 4 is disposed in the center and an escape hole 5 of the stick is opened at the terminal end of the part which accepts the stick.

The shape of the monolith adsorbent is not limited to the above and can be readily molded into a form of a disk, a form of a rod, a form of a cup and so on in accordance with the target use thereof.

EXAMPLE 1

Figure 1:
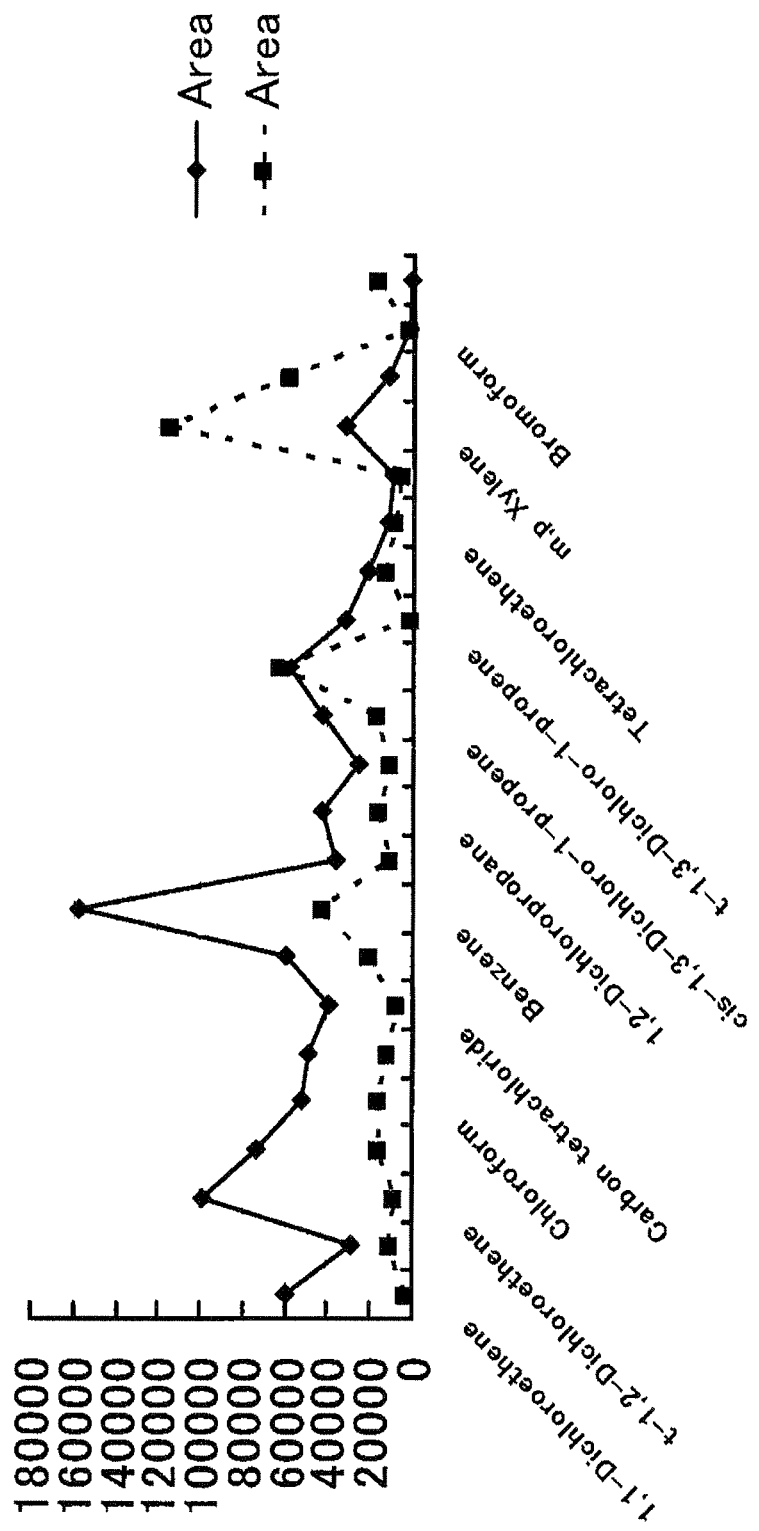
FIG. 1 is a graph which compares desorption performance of an activated carbon containing monolith structure body.

The comparison between adsorption with only a monolith structure body and the monolith structure body containing an activated carbon is described referring to FIG. 1.

1) Activated carbon containing monolith structure body (treated with ODS; not subjected to coating treatment): solid line
2) Only monolith structure body (treated with ODS; not subjected to coating treatment): dotted line (Experimental Method)

The monolith adsorbents 1) and 2) were installed in the upper part (headspace) of a 5 ml screw tube (fixed to a gaseous phase part), and a volatile organic compound (25 μg/mL) was injected into the screw tube, and the screw tube was sealed and left untouched for 10 minutes, and then the respective monolith adsorbents were eluted with 100 μL of methanol and analyzed by 1 μL GCMS to compare the area value.

In this experiment, the content of the activated carbon was 1.5% (weight ratio), the particle diameter was 3 to 10 μm, the through-pore size was 5 to 10 μm, and the surface area of monolith adsorbents was 600 to 700 $m^2/g$.

(Results)

When activated carbon was contained, good adsorbing effects were generally observed. Particularly for 1,1-Dichloroethene to 1,2-Dichloroethane (low boiling point components having boiling point 32° C. to 83.5° C.), the effect of containing activated carbon is clear (FIG. 1).

EXAMPLE 2

Analysis of Volatile Organic Compound Samples Experimental Method

15% salt was added to 40 mL of water to adjust the concentration to 2 ppb/40 mL. 19.4 mg of silica monolith having a through-pore of 5 to 15 μm and containing activated carbon whose particle diameter was 10 μm or less was put in a vial and stirred for 10 minutes.

Then the silica monolith was subjected to extraction with 100 μL of methanol (exposed to supersonic wave for ten minutes for extraction).

1 μL of the extract was analyzed with GCMS in SIM mode in splitless condition.

The absolute injection amount to GCMS was 0.8 μg.

(Results)

Figure 5:
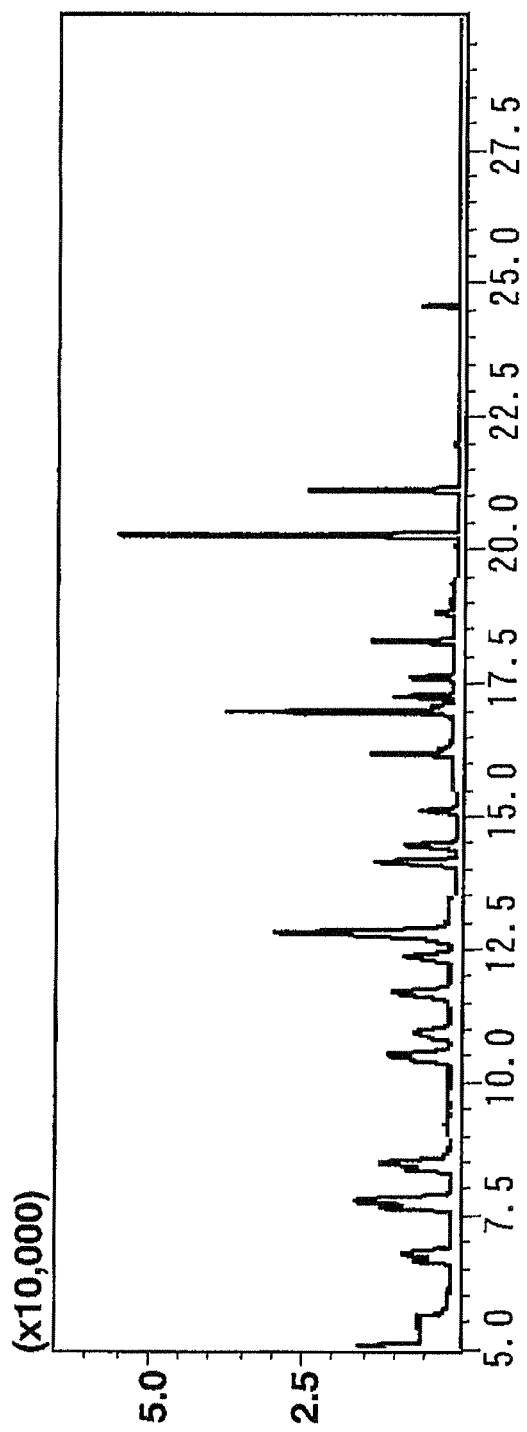
FIG. 5 is a chromatogram analyzing a volatile organic compound in an example of the present invention.

As shown in FIG. 5, very good chromatography was obtained. There are no problems in sensitivity at all.

EXAMPLE 3

Analysis of Low Concentration Volatile Organic Compound Samples

It was confirmed whether in analysis of tetrachloride nitrogen having a low concentration of 0.2 ppb (0.2 μg/L) the detection thereof was possible or not by the method of the present invention.

(Experimental Method)

15% salt was added to 40 mL of water to adjust the concentration to 0.2 ppb/mL.

22 mg of silica monolith having a through-pore of 5 to 15 μm and containing activated carbon whose particle diameter was 10 μL or less was put in a vial and stirred for 10 minutes.

Then the silica monolith was subjected to extraction with 100 μL of methanol.

1 μL of the extract was analyzed with GCMS in SIM (selected ion monitor) mode in splitless condition. The absolute injection amount to GCMS was 0.08 ng.

(Results and Consideration)

Figure 6:
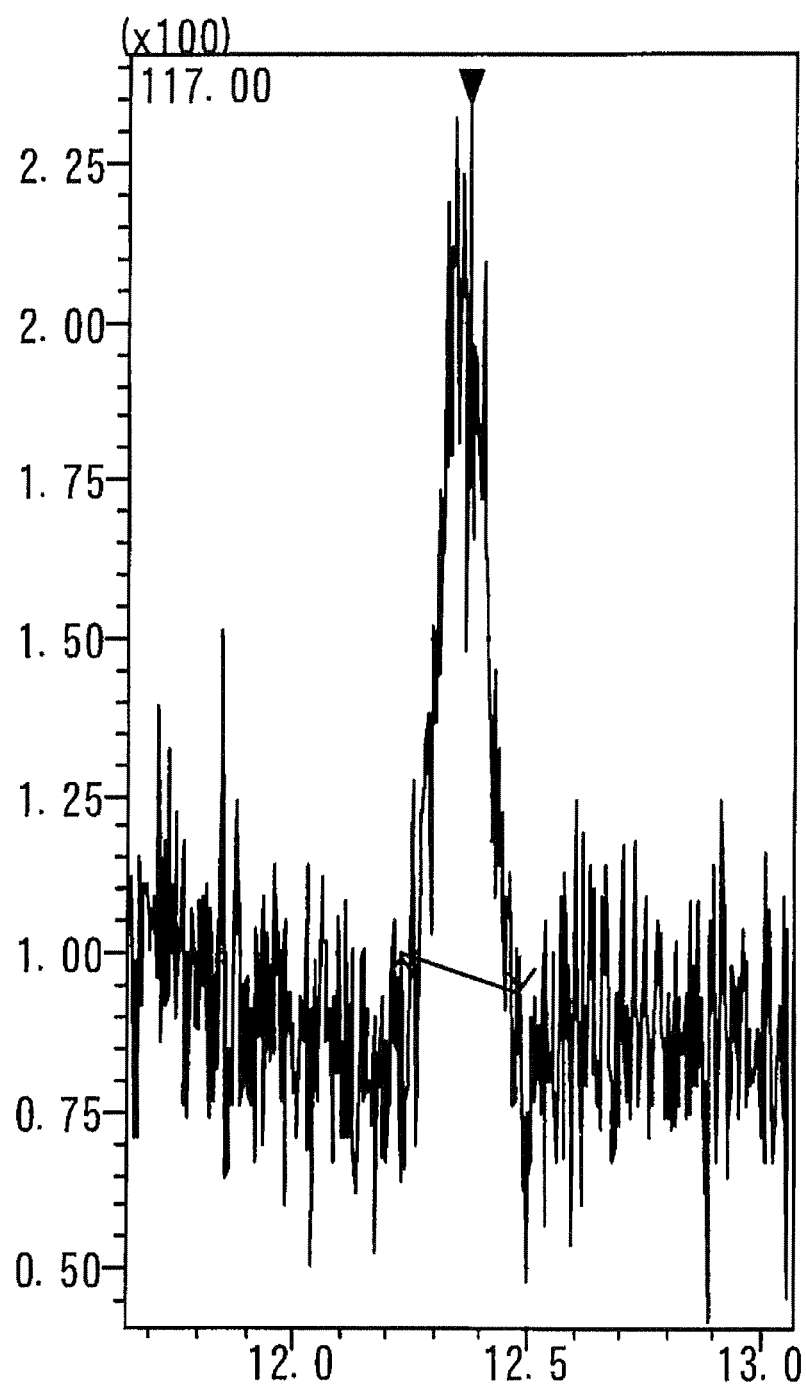
FIG. 6 is a chromatogram analyzing carbon tetrachloride in an example of the present invention.
Figure 7:
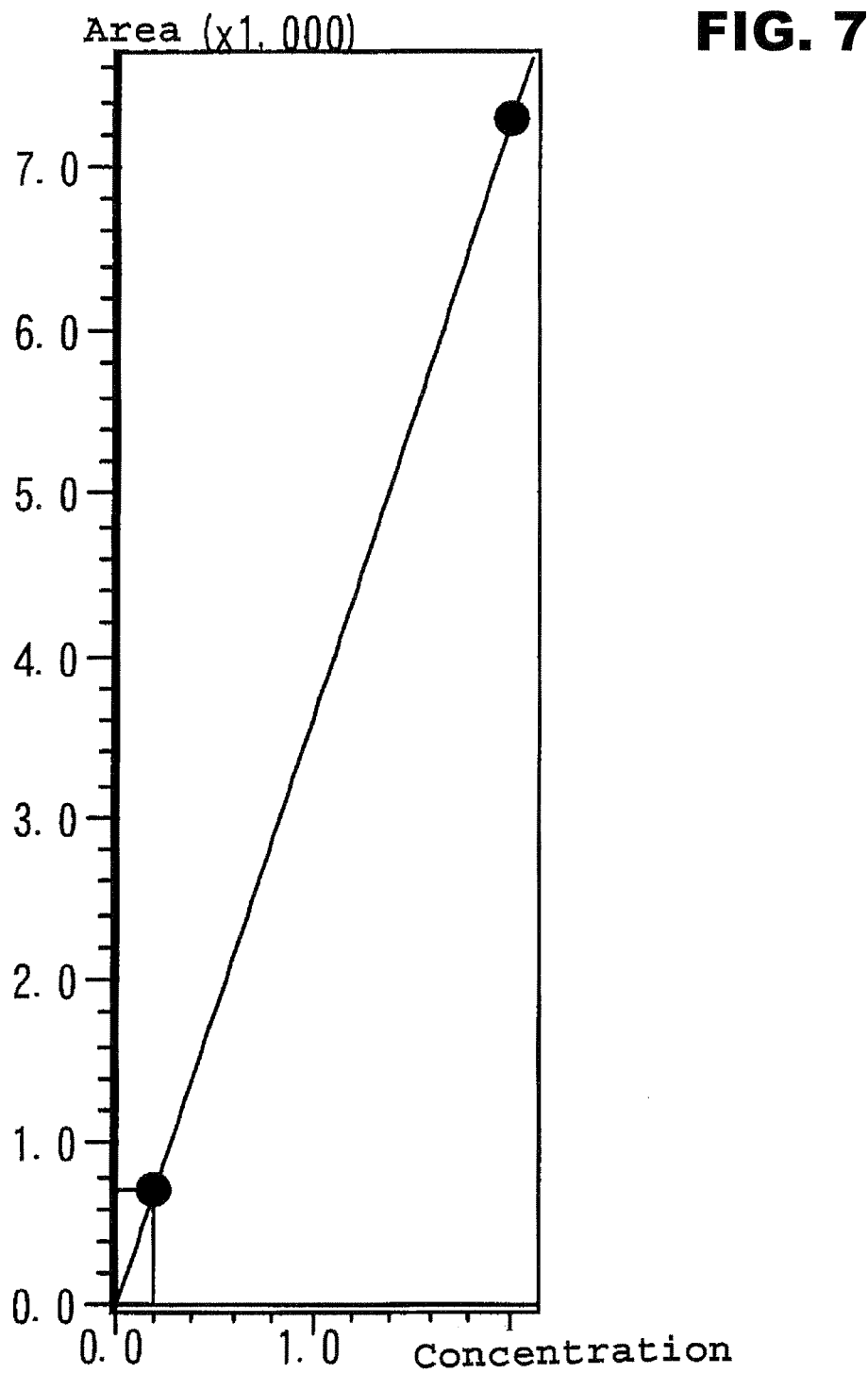
FIG. 7 is a chromatogram analyzing carbon tetrachloride in an example of the present invention.

Confirmation of the detection was possible although it was close to SN limitation. (FIG. 6, FIG. 7).

It can be judged from this experiment that confirmation is possible to judge ON/OFF for screening even by solvent extract. Naturally, in order to enhance the precision and the sensitivity, 100 times of this case could be obtained by thermal desorption method since the injection amount was 1 μL, which sensitivity has sufficient performance.

EXAMPLE 4

Comparison Among Activated Carbon, Graphite and ODS Alone

Comparison of elution amount of 2 ppb volatile organic compound (same concentration) among a. activated carbon containing silica monolith treated with ODS
b. graphite containing silica monolith treated with ODS
c. silica monolith treated with ODS The particle diameter of the activated carbon was 10 μm or less, the surface area of the graphite was about 100 $m^2/g$, and the through-pore of the monolith structure body was 5 to 15 μm.

(Sample 1)

①: 1,1-Dichloroethene, ②: Dichloromethane, ③: t-1,2-Dichloroethene

Figure 8:
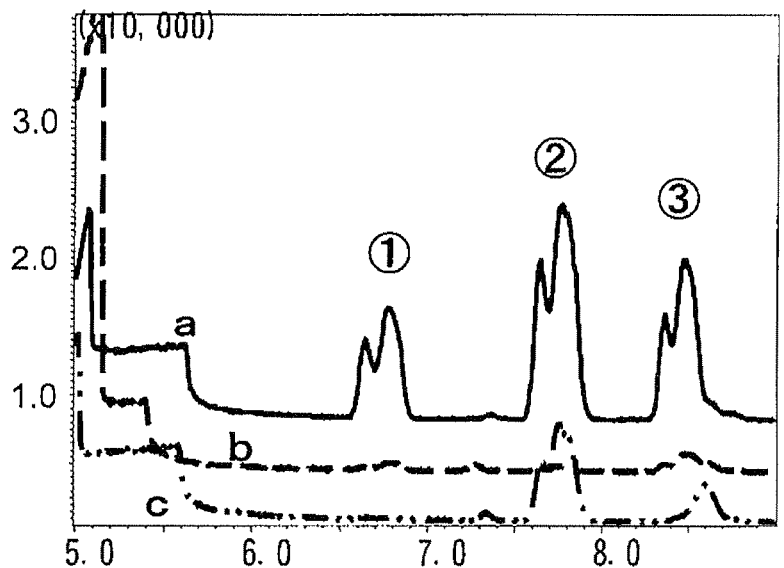
FIG. 8 is a chromatogram illustrating the retention of samples in an example of the present invention.

In the low boiling point range (sample 3 mentioned above), the superiority of activated carbon is remarkable. (FIG. 8)

(Sample 2)

Figure 9:
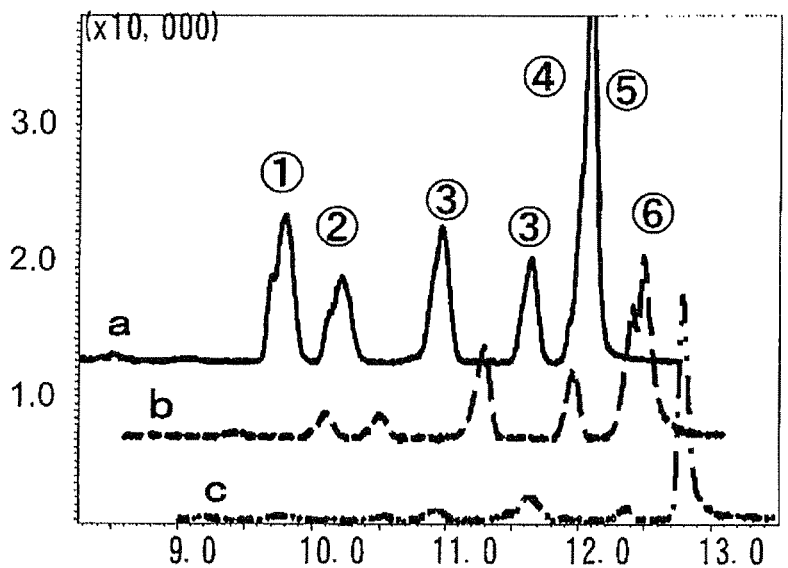
FIG. 9 is a chromatogram illustrating the retention of samples in an example of the present invention.

①: cis-1,2-Dichloroethene, ②: Chloroform, ③: 1,1,1-Trichloroethane, ④: Carbontetrachloraide, ⑤: 1,2-Dichloroethane, ⑥: Benzene (FIG. 9)

(Sample 3)

Figure 10:
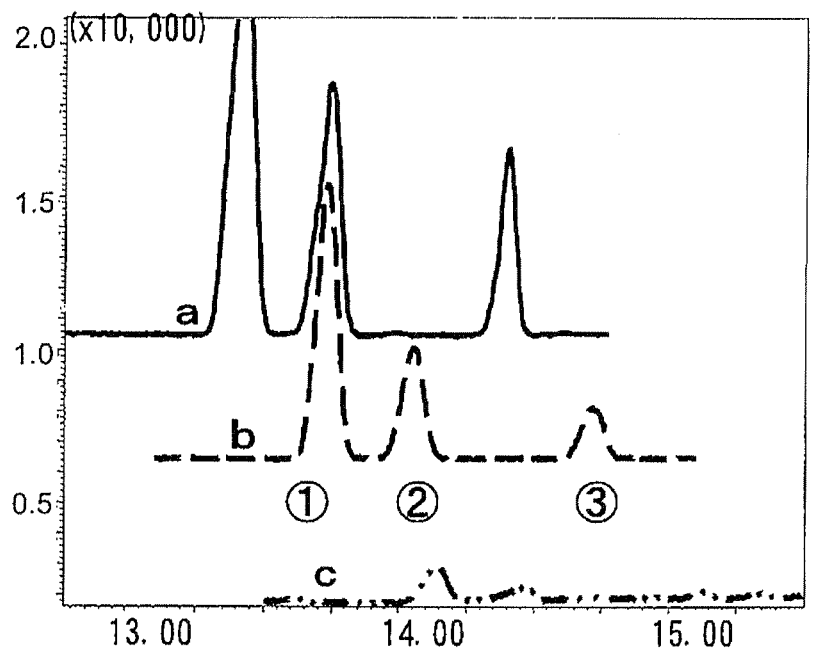
FIG. 10 is a chromatogram illustrating the retention of samples in an example of the present invention.

①: Trichloroethene, ②: 1,2-Dichloropropane, ③: Bromodichloromethane (FIG. 10)

(Sample 4)

Figure 11:
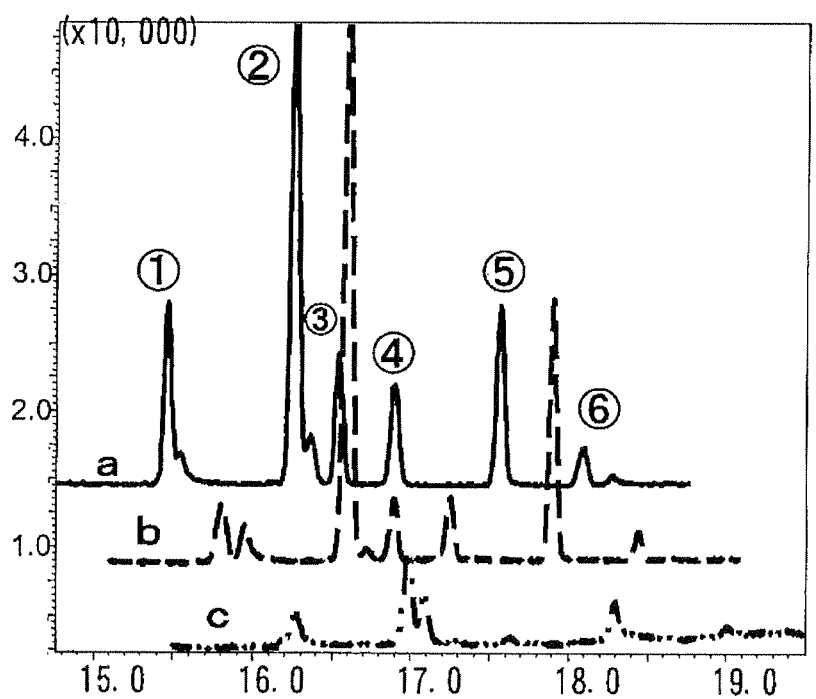
FIG. 11 is a chromatogram illustrating the retention of samples in an example of the present invention.

①: cis-1,3-Dichloro-1-propene, ②: Toluene,t-1, ③: 3-Dichloro-1-propene, ④: 1,1,2-Trichloroethane, ⑤: Tetrachloroethene, ⑥: Dibromochloromethane It can be confirmed that the graphite containing system showed retaining comparable to those of activated carbon for toluene having a cyclic structure. In accordance with the characteristics of the graphite carbon (FIG. 11).

(Sample 5)

①: m,pXylene o, ②: Xylene

Figure 12:
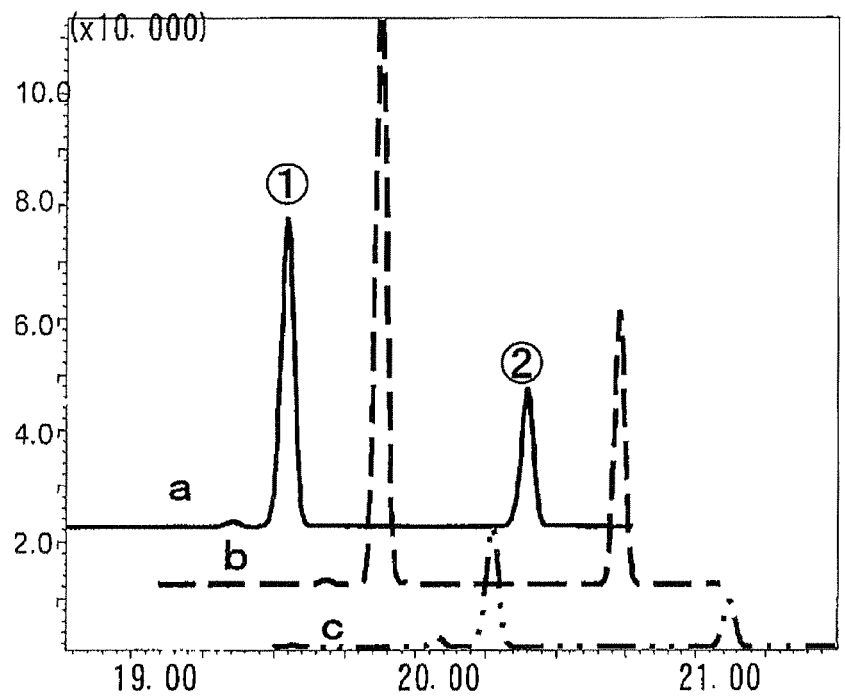
FIG. 12 is a chromatogram illustrating the retention of samples in an example of the present invention.

It can be confirmed that retaining by graphite carbon which is strong for cyclic structures is strong. (FIG. 12)

(Sample 6)

Bromoform

Figure 13:
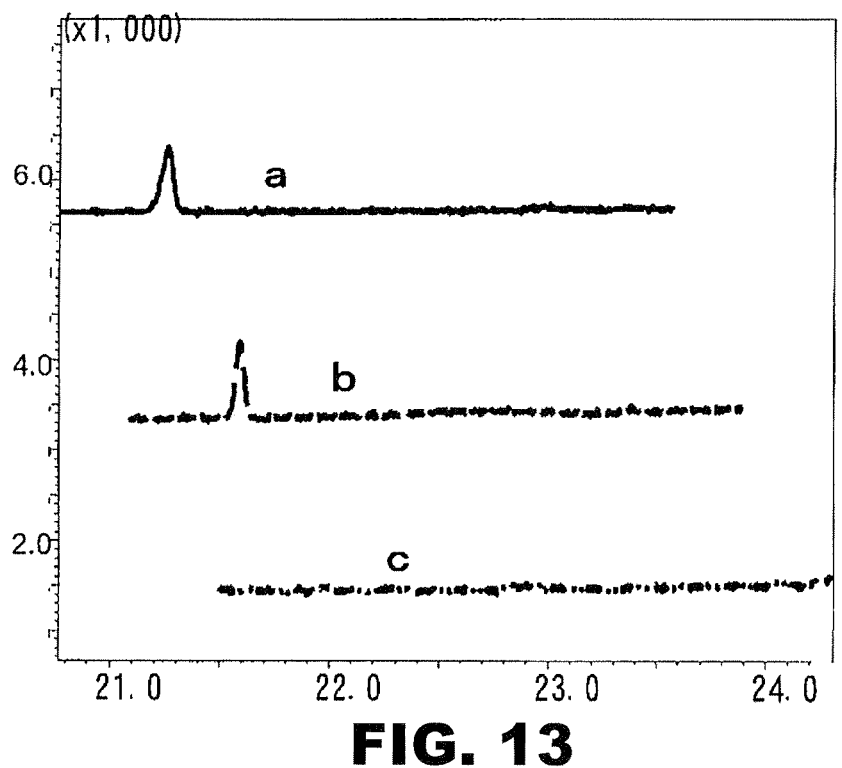
FIG. 13 is a chromatogram illustrating the retention of samples in an example of the present invention.

There are no difference between activated carbon and graphite. (FIG. 13)

(Sample 7)

1,4-Dichlorobenzene

Figure 14:
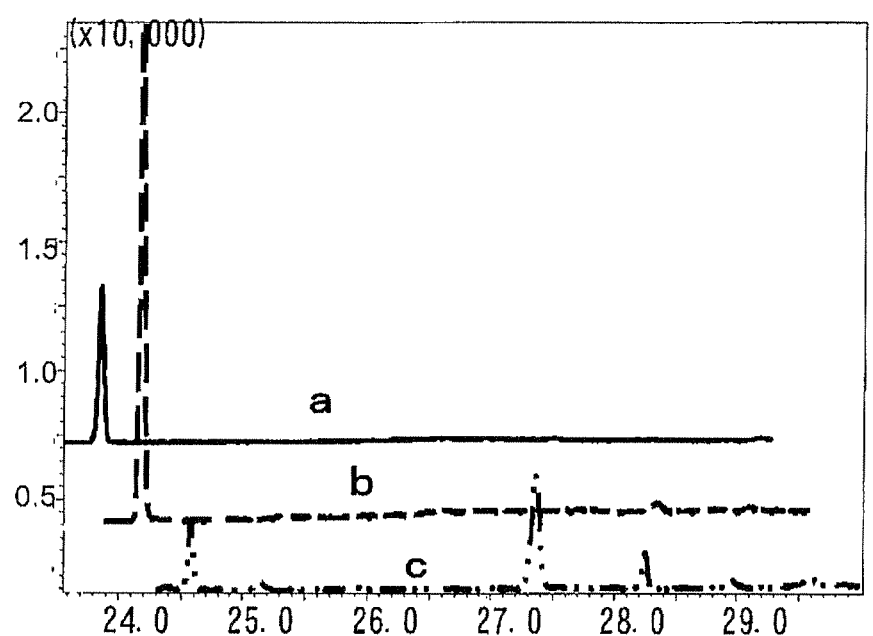
FIG. 14 is a chromatogram illustrating the retention of samples in an example of the present invention.

Superiority of graphite carbon which is strong for cyclic structures is clear (FIG. 14).

Both of the active carbon and graphite carbon have characteristics and the active carbon was advantageous for low boiling point components whereas the graphite was advantageous for the component having cyclic structures. It can be predicted from this that the two kinds could be mixed with multi-bed for the analysis of the present invention for volatile organic compounds.

If several kinds of adsorbing materials were mixed with the monolith in accordance with the purpose, those suitable for the target can be easily prepared and provided with hydrophobicity owing to ODS, besides, useless dry purge can be simplified and thus the present method would be a adsorbing method having an extremely high potential. In addition, due to the structure having through-pores, which is an advantage of the monolith structure, the reagents are easy to pass through the inside of the adsorbing material so that the reagents are easy to adsorb and the solvent is also easy to pass through likewise, and accordingly, the extraction is enabled with a small amount of a solvent.

EXAMPLE 5

Volatile Organic Compound Samples 1,1-Dichloroethene,Dichloromethane,t-1,2-Dichloroethene,cis-1,2-DichloroetheneChloroform,1,1,1-Trichloroethane,CarbonTetrachloride,1,2-DichloroethaneBenzene, Trichloroethene,1,2-Dichloropropane, Bromodichlomethane,cis-1,3-dichloro-1-propene,Toluene,t-1,3-Dichloro-1-propene,1,1,2-Trichloroethane, Tetrachloroethene,Dibromochloromethane,m,pXylene,o, Xylene,Bromoform,1,4-Dichlorobenzene The respective components were added to a 40 mL aqueous solution to which 15% NaCl was added to adjust the concentration to 2 ppb. The following monolith adsorbents were put in the solution and stirred for 30 minutes.

1) monolith structure body whose surface was treated with ODS 2) activated carbon containing monolith structure body whose surface was treated with ODS 3) monolith structure body containing activated carbon and graphite wherein the surface of the structure body was treated with ODS 4) monolith structure body containing activated carbon, graphite and molecular sieve wherein the surface of the structure body was treated with ODS Then, the above monolith adsorbents were taken out and eluted with 100 μL of a solvent and 1 μL thereof was injected to GCMS in SIM mode. The absolute retention volume of each component was 40 mL and therefore 80 ng is held according to the calculation. Accordingly, when diluted to 100 μL and 1 μL was injected, the content is 0.8 ng.

Therefore, a standard sample was prepared so that 0.8 ng was contained in 1 μL of the standard sample and injected to obtain an area value for comparing the recovery ratios.

Figure 15:
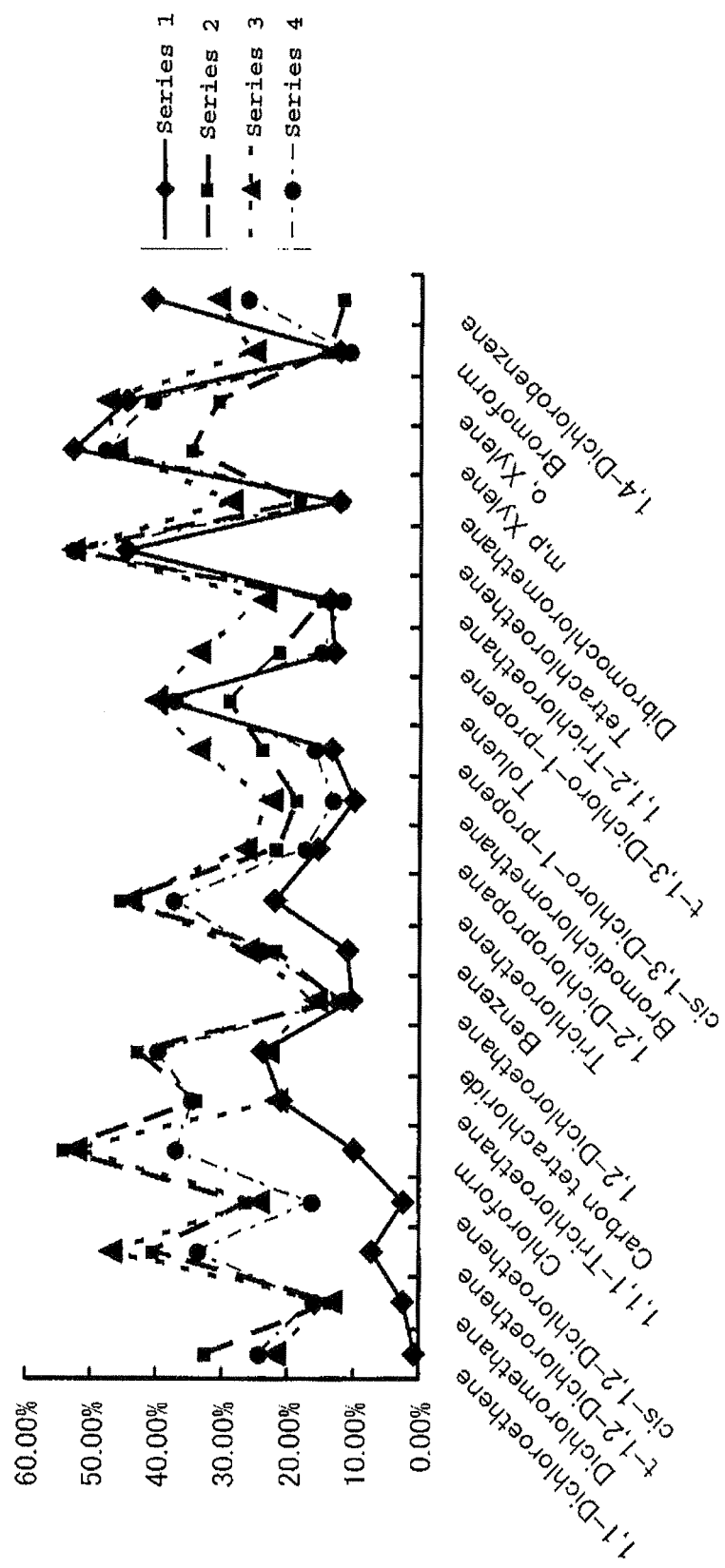
FIG. 15 is a chromatogram comparing the retention of samples in an example of the present invention.

It can be understood that effects by the addition of the adsorbing materials were obtained for the recovery ratios of 1,1-Dichloroethene, Dichloromethane, t-1,2-Dichloroethene, cis-1,2-Dichloroethene, Chloroform which are low boiling point components since those containing the adsorbing materials resulted in 5 times higher values (FIG. 15).

EXAMPLE 6

Graph in which a Liquid Phase of OV1 is Applied to the Whole Adsorbing Materials as One of the Surface Treatments Components in the sample and the concentration method are the same as in EXAMPLE 5, and the stirring time is 60 minutes.

C,G,ODS (monolith structure body containing activated carbon and graphite wherein the surface of the structure body was treated with ODS)

C,G,ODS,OV1 (OV1 was applied to the whole adsorbing materials mentioned above)

Figure 16:
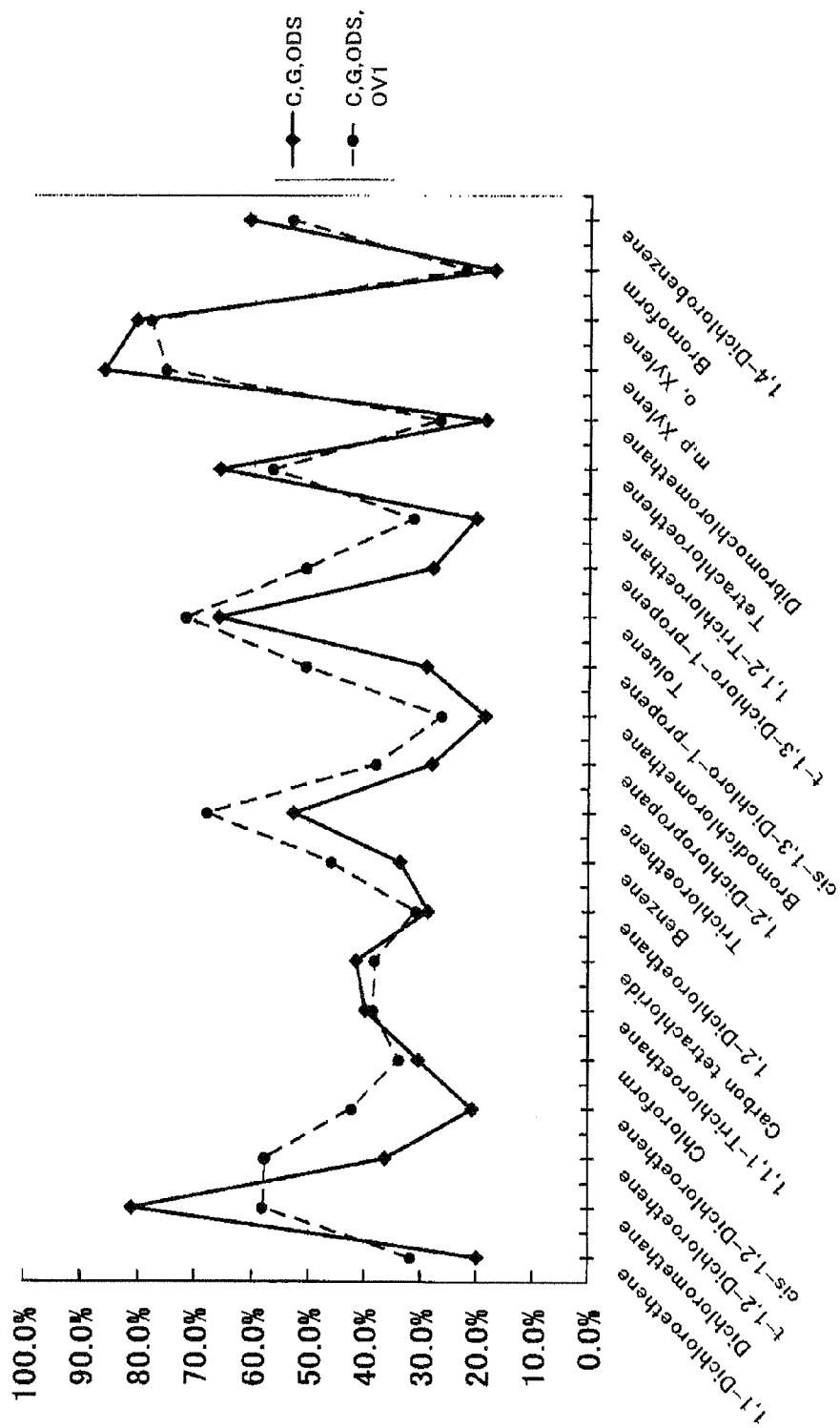
FIG. 16 is a chromatogram comparing the retention of samples in an example of the present invention.

Recovery ratio of around 80% was obtained in aromatic hydrocarbons including m,p,o-xylene by using the technology of the present invention and it can be understood that the retaining was not performed by phase equilibrium but complete adsorption (FIG. 16).

EXAMPLE 7

The monolith adsorbent 23 and the solvent 24 were installed within the vial 22 of the auto-sampler 21. Since the monolith adsorbent 23 has a structure 17 having a through-hole 25 inside thereof and accordingly, the sample can be extracted within the vial 22 and injected just as it is into GC with an auto-sampler, this system is very simple and convenient.

Figure 17:
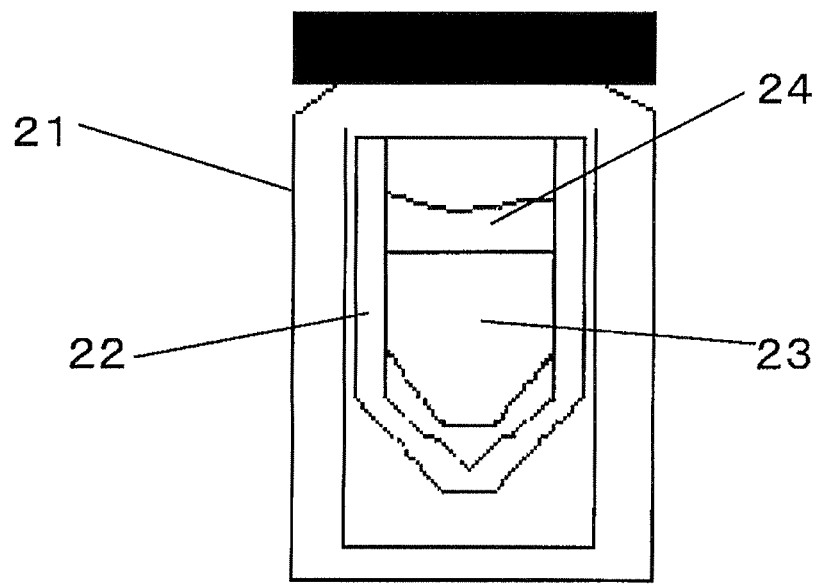
FIG. 17 is a schematic view illustrating the usage in an example of the present invention.
Figure 18:
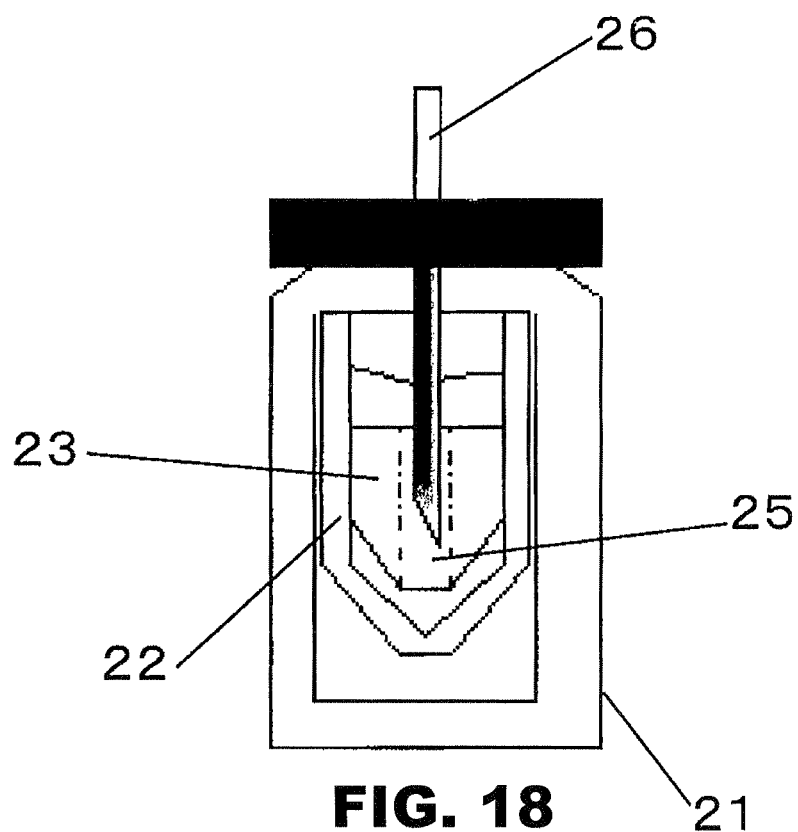
FIG. 18 is a schematic view illustrating the usage in an example of the present invention.

At first, the sample held in the monolith adsorbent 23 is extracted with a solvent 24. The extraction can be performed only by immersing the monolith adsorbent 23 in the solvent 24, but a supersonic wave can be optionally applied. The extracted components were sucked with a syringe 26 and analyzed in GC (FIG. 17, FIG. 18).

EXAMPLE 8

It often takes time in normal PDMS-coated SPME (not a monolith adsorbent) to retain the sample. In the case of a high boiling point component (plasticizer, etc.) in particular, the sample water temperature requires heating of around 60 to 70° C., and general technique comprises impregnation for around 30 minutes to 60 minutes to adsorb and retain the sample in the PDMS retaining part.

However, this length of time is problematic in rapid analysis. Therefore, technique to adsorb in a short time was investigated.

1) Adsorption Method 1

The monolith adsorbent of the present invention (activated carbon content: 1.5%) 32 was formed in accordance with the taper of the container 31. A container having a tapered part at one end and an opening on the tip thereof was formed and the monolith adsorbent was accommodated in the container 31. A sample having a plasticizer (dibutyl hydroxytoluene (BHT antioxidant), dibutyl phthalate (DBP), adipic acid diester (DOA)) in a concentration of 20 ppb and adjusted to 5 mL was formed (at room temperature) and the monolith adsorbent 32 was press fixed with a fixture 35 with a screw in the outer circumference thereof. The sample was injected through and held in the monolith adsorbent 32 with a syringe 33. The solution injected through was received with a beaker 34 and the sample injected was sucked off, and pumping was repeated five times so that the components might be held.

Figure 19:
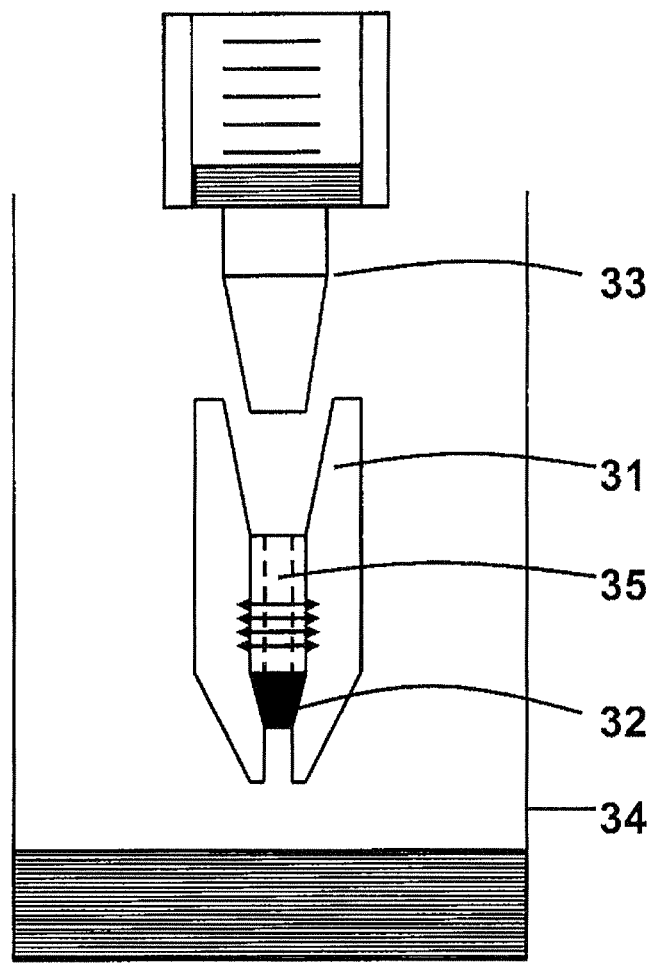
FIG. 19 is a schematic view illustrating the usage in an example of the present invention.

After the target components were held, 100 μL of a solvent (dichloromethane) was passed through the monolith adsorbent 32 and the flow was received with a beaker 34 in the same way as above, and pumping was repeated to perform elution (FIG. 19).

Adsorption Method 2

Figure 20:
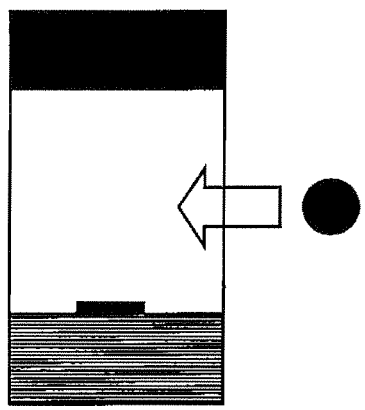
FIG. 20 is a schematic view illustrating the usage in an example of the present invention.

For comparison with the adsorption method 1 mentioned above, 5 mL of a sample was injected to a 20 mL vial as shown in FIG. 20 and a monolith adsorbent in the form of a disk was floated thereon and stiffing was performed at 70° C. for 30 minutes to perform retaining. After the retaining was finished, the disk was taken out and subjected to elution by a supersonic wave with 100 μL of dichloromethane.

Figure 21:
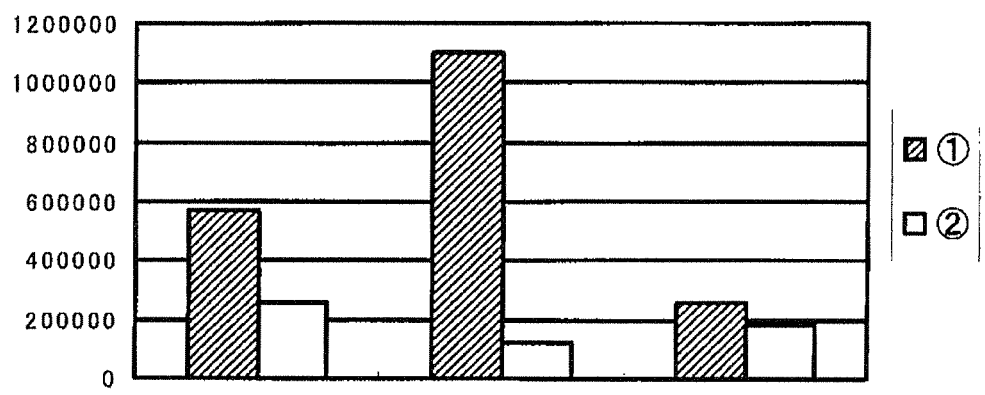
FIG. 21 is a graph illustrating the usage in an example of the present invention.

The recovery of the plasticizer by the adsorbing methods 1 and 2 mentioned above are shown by the respective area values ① and ② (FIG. 21).

In the adsorption method 1, the results as shown above (high recovery ratio of plasticizers (BHT/DBP/DOA)) were obtained by a short time and simple adsorbing method of performing pumping of the sample solution five times as compared with the adsorption method 2 in which stiffing for 30 minutes was performed.

In addition, whereas the normal solid phase is eluted with around 5 mL of a solvent and the extract is re-concentrated to around 1 mL, the present invention, when the adsorbed target component is eluted with a solvent, requires only as small an amount of solvent as around 100 μL as in the adsorption method 1 without re-concentration to perform elution successfully. This seems to be the effect of pumping and the through-pore of the monolith.

In addition, efficient adsorption is enabled with less amount of a sample solution than the conventional methods by repeatedly flowing the sample liquid through the adsorbing material by pumping.

2) Effect of Containing Activated Carbon in Adsorption Method 1

Figure 22:
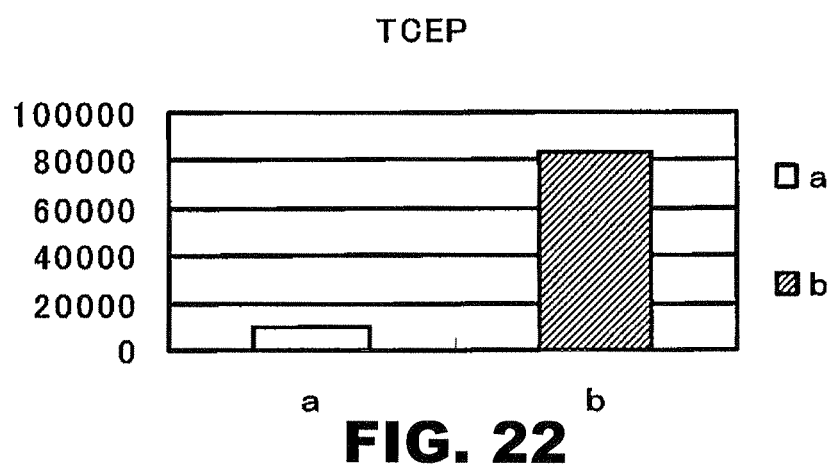
FIG. 22 is a graph illustrating the usage and effect in an example of the present invention.

The results of analysis of TCEP (tris(2-chloroethyl)phosphate) in water are shown below for demonstrating the effect of containing activated carbon in the adsorbing method by pumping mentioned above.

a: silica monolith the surface of which was treated with ODS b: silica monolith which contained 3% activated carbon and the surface of which was treated with ODS The area values reveal that an effect of around 10 times larger is resulted by containing activated carbon (FIG. 22).

As is shown by the above results, it can be understood that the silica monolith ODS alone does not give satisfactory results with regard to retaining of a low boiling point component, and after all a method of containing an adsorbing material such as active carbon is an effective method.

EXAMPLE 9

Analysis of Mold Odor

Mold odor is in extremely low concentration; the lower limit value for detecting 2-MIB, geosmin by the solid-phase extraction method is a low concentration as low as 0.002 μg/L=0.002 ng/mL=2 pg/mL=2 ppt.

In addition, the effects of contaminant components are significant; due to the effects of salt blank in the salting-out and contaminating components in the river water, analysis of mold odor is difficult.

Actually, there are cases where the target component in the sample and contaminations have the same mass number as the target component and thus cannot be distinguished, even in GCMS and SIM methods.

The method using the present invention is described.
(Analysis Flow)
1. 25% aged NaCl is added to the analyte water.
2. 3 pieces of activated carbon-containing monolith adsorbent in the form a disk are added to a vial containing 100 mL of the analyte water.
3. The vial is stirred in a constant temperature water tank having a stirring function at 65° C. for 60 minutes.
4. The activated carbon-containing monolith adsorbent in the form of a disk is taken out and wiped off the attached water by using kimwipe.
5. The monolith adsorbent is immersed in 1 mL of dichloromethane and eluted with a supersonic wave for around 15 minutes.
6. 1 mL of the sample is concentrated to 100 μL by $N_2$ purge. The analyte sample having a final volume of 100 μL is obtained.

(Experiment 1 Recovery Ratio Test)

25% aged NaCl was added to 100 mL of mineral water. 1 μL of 2-MIB and geosmin having a concentration of 200 ng/mL was added thereto, which was held by the disk and concentrated and finally 100 μL of the analyte sample was obtained. The absolute amount is 200 pg/100 μL and becomes 2 pg/μL when 1 μL is injected.

For the purpose of comparison, 200 ng/mL of a standard sample was diluted 100-fold so that the absolute amount might be the same (1 μL of 2 ng/mL equals to 2 pg/mL), and area values were obtained by direct GCMS, SIM method and compared to the area value of the sample held by the above disk and thereby to determine the recovery ratio.

(Experimental Result 1)

Figure 23:
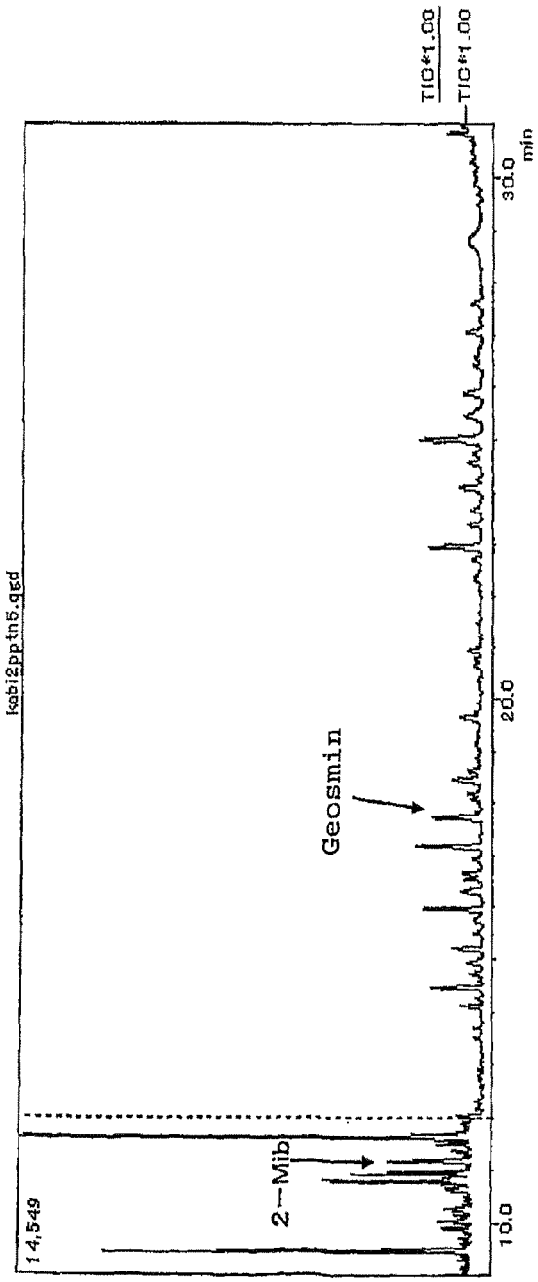
FIG. 23 is a graph comparing the recovery ratio between an example of the present invention and a comparative article.

Recovery ratio, 2-MIB: 76.95%, geosmin: 72.05% (FIG. 23)

Reproducibility (n5) 2-MIB: 6.22%, geosmin: 6.57%

(Experiment 2 Confirmation of the Influence of Contaminant in the Case of River Water)

An experiment to confirm if 2-MIB, geosmin can be determined in the situation where contaminants in the river water are present 1. NaCl was added so as to have a concentration of 25%, and a mold odor standard sample was added to 100 mL of river water so as to be 2 ppt concentration.
2. For comparison, NaCl was added to pure water so as to have a concentration of 25%.
3. A standard sample adjusted with a dichloromethane solvent so that the absolute amount might be the same concentration of 200 ppt.

Figure 24:
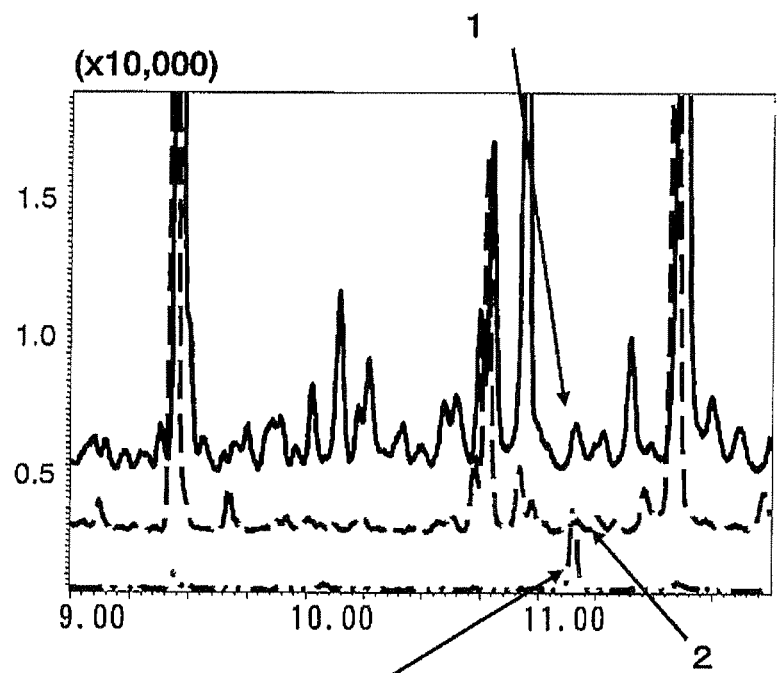
FIG. 24 is a chromatogram analyzing river water in an example of the present invention.
Figure 25:
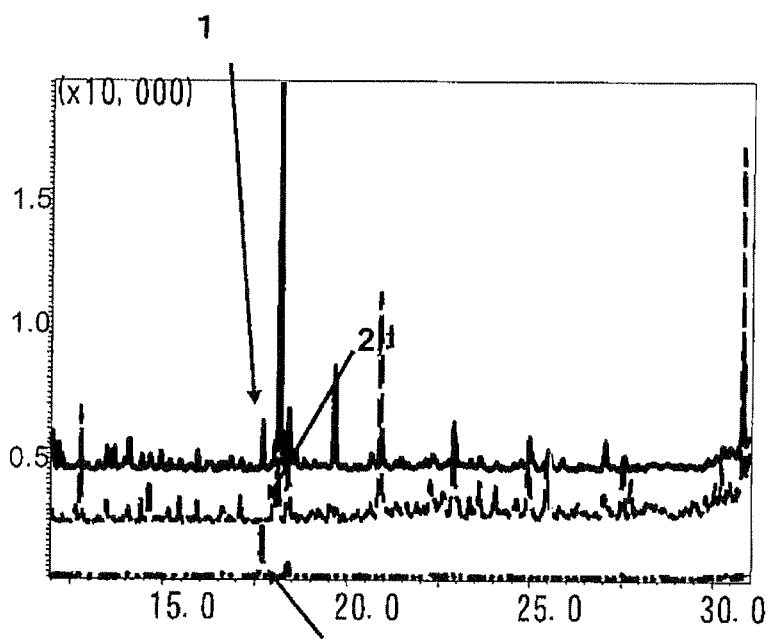
FIG. 25 is a chromatogram analyzing river water in an example of the present invention.

It was examined whether the determination could be performed in the actual river water. The possibility that 2 mib, geosmin occurred was low since alga did not occur in the winter season but mold odor STD was added to river water so as to be 2 ppt concentration and comparison was performed to determine whether 2-MIB (FIG. 24), geosmin could be confirmed in river water in which there was high level of contaminants. 2-MIB in the river water is difficult but the confirmation thereof is possible. Confirmation of geosmin does not have any problem (FIG. 25).

EXAMPLE 10

Analysis of Chemical Substance in the Room

There have been a number of report reports on the condition that the residents suffer from various physical bad conditions (so-called sickhouse syndrome) due to room air contamination by chemical substances in newly constructed or reconstructed houses or buildings, which are attributable to high airtightness of the houses and the use of building materials and interior materials emitting chemical substances.

Various chemical substances are put on the guideline of Ministry of Health, Labour and Welfare and the guideline values thereof have been also determined Therefore, technology for assaying chemical substances in the air with good reproducibility is demanded.

(Analysis Technique)

The volatile organic compounds are sampled using any one the three methods: solid-phase adsorption/solvent extraction method, solid-phase adsorption/heating desorption method and container adsorption method. Analysis is performed by gas chromatograph mass spectroscopy (GC-MS).

By the suction method (active method), the most sensitive heating desorption method is used, and in the diffusion method (passive method), the solvent extraction method (with carbon disulfide) is more commonly used than the heating desorption method.

The experiment flow is described below.
1. Sampling
Suction flow rate: 1.0 L/minute
2. Sample introduction
PTV: 40° C., 16° C./second, 280° C. (5 minutes)
3. Column
Inert Cap 5MS, 0.25 mm ID×30 M, df=0.25 μm
4. Oven temperature
40° C. (3 minutes), 20° C./minute, 280° C. (5 minutes)

Sample introduction is performed with a special thermal desorption device in the conventional capillary GC sample introduction method by the solid-phase adsorption/thermal desorption, and cryofocussing with liquid nitrogen is essential for attaining high separation among toluene and xylene isomers (ortho-, meta- and para-xylene). On this account there is a disadvantage that it takes cost and time per analysis.

Figure 26:
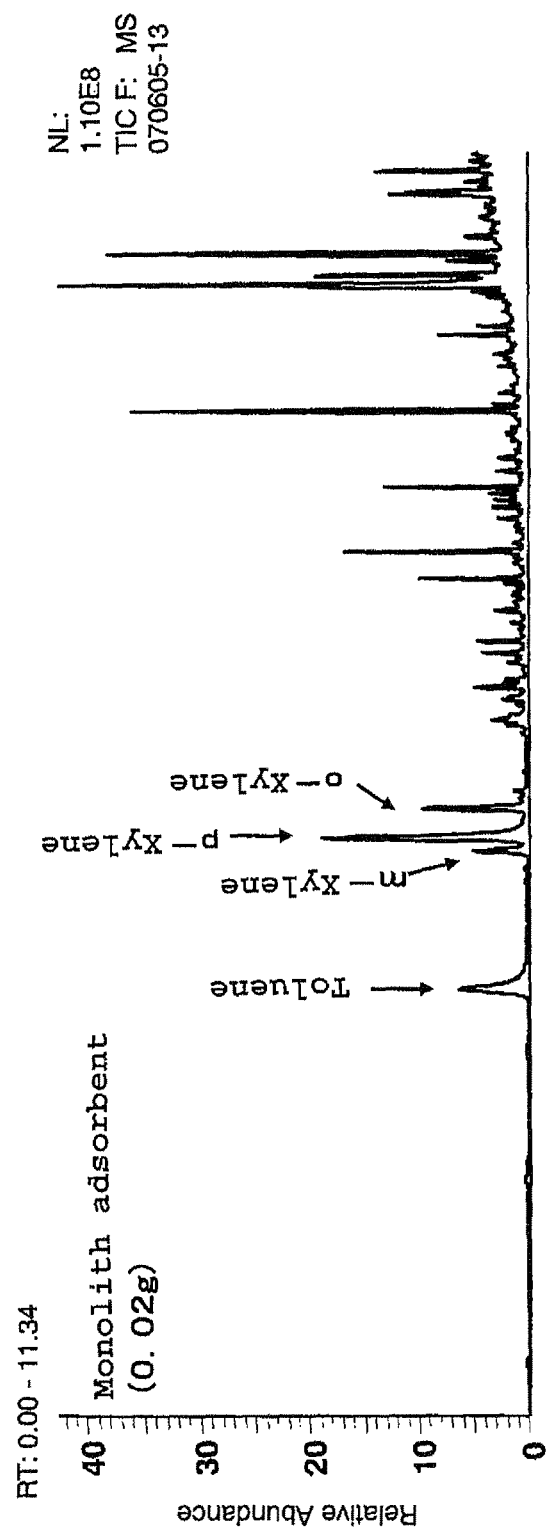
FIG. 26 is a chromatogram analyzing chemical substances in the room in an example of the present invention.
Figure 27:
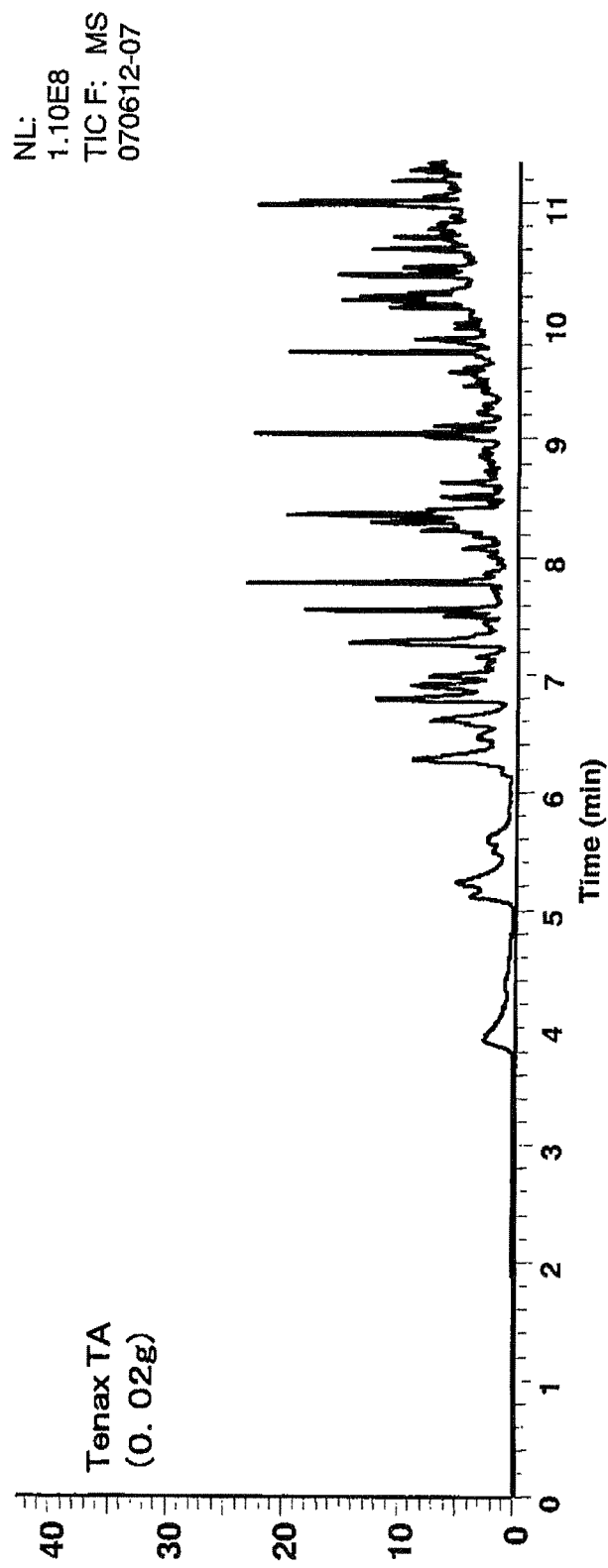
FIG. 27 is a chromatogram analyzing chemical substances in the room in an example of the present invention.

In contrast, the analysis by monolith adsorbent uses PTV injection port and attains sufficient separation of toluene and xylene isomers without using cryofocussing. This leads to reduction of the analysis cost, shortening of the analysis time and improvement in the precision of analysis in comparison with the conventional methods (FIG. 26, FIG. 27).

EXAMPLE 11

Effect of Monolith Adsorbent by Passive Sampling

A gardenia was covered with a bag and the monolith adsorbent and SPME were exposed in that so as to perform passive sampling (exposure for 3 hours). The monolith adsorbent was solvent extracted with 1 mL of dichloromethane after the exposure and the extract was concentrated to 100 μL in volume and 1 μL thereof was injected to GCMS. SPME was injected to GCMS just as it is after the exposure.

Figure 36:
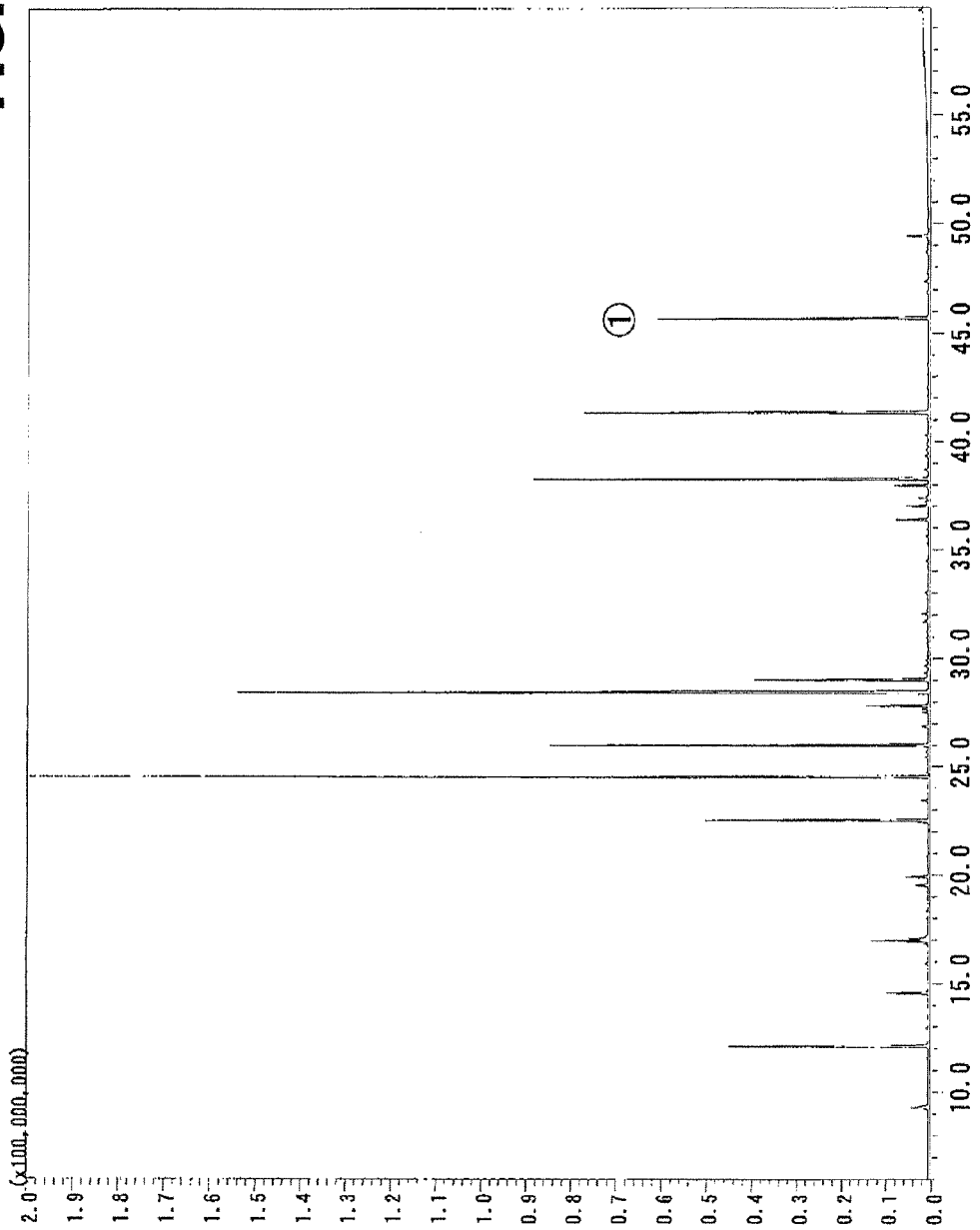
FIG. 36 illustrates the sampling effect by the present invention.
Figure 37:
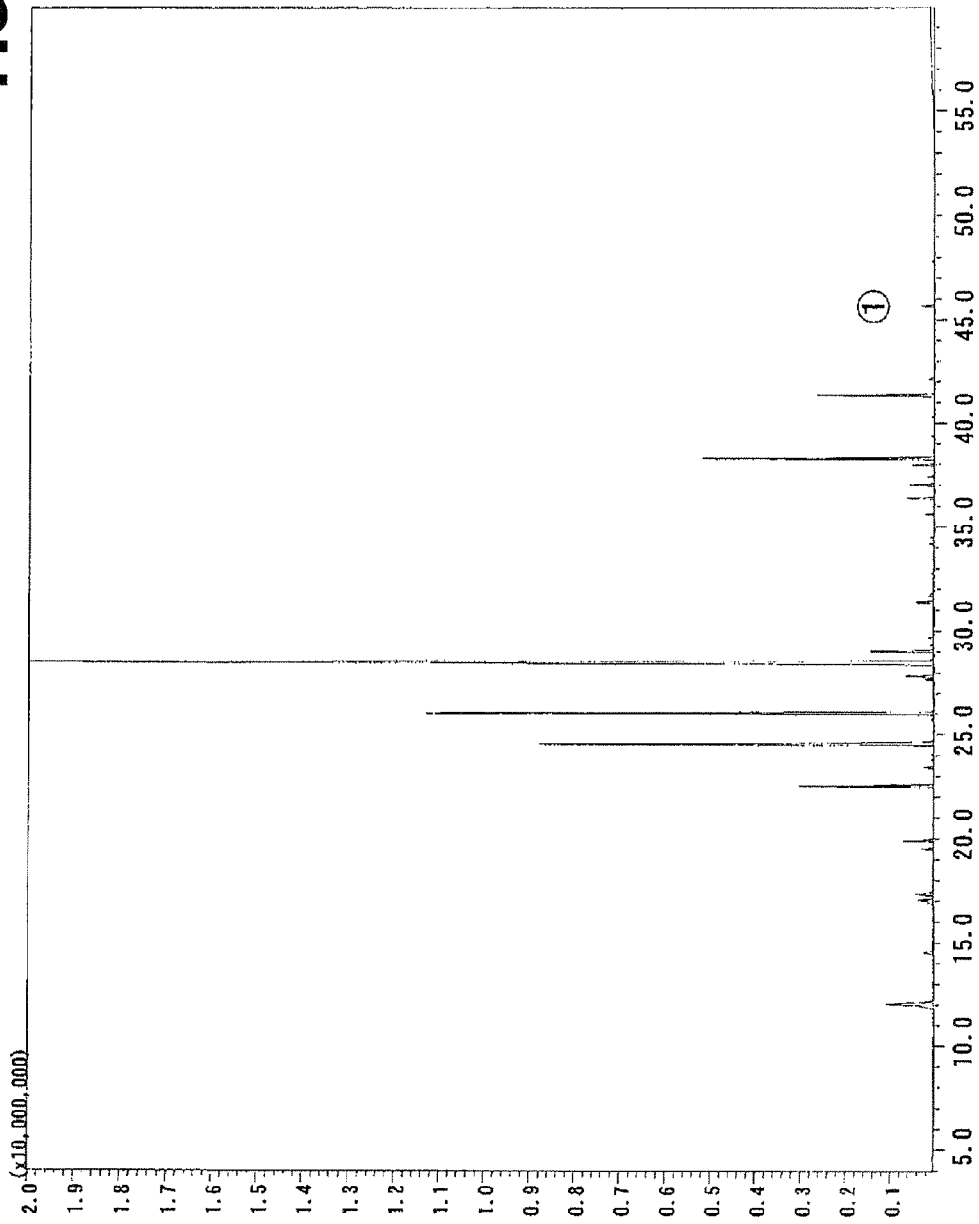
FIG. 37 illustrates the sampling effect by the present invention.

According to the sampling by the monolith adsorbent of the present invention, indole (①in FIG. 36) can be confirmed well (FIG. 36).

It can be understood that since the monolith adsorbent has an excellent sampling ability, even when the extract is diluted 100-fold in the solvent extract, the sensitivity thereof is comparable to the thermal desorption (SPME) which injects the total volume.

EXAMPLE 12

Experiment to Confirm whether Sufficient Extraction of Sample is Possible or not by Flowing Sample through Monolith Adsorbent
1. Preparation of Sample
(1) Sample Aqueous Solution An aqueous solution containing 2-methylisoborneol (2-MIB) and geosmin in a concentration of 1.0 ng/L was prepared.
(2) Sample for Confirming Recovery Ratio A methanol solution containing 2-methylisoborneol (2-MIB) and geosmin in a concentration of 1 ng/μL was prepared.
2. Extracting Method 100 mL of the sample aqueous solution was sampled with a syringe, and directly flowed through a silica monolith type solid phase extractant which was a monolith adsorbent of the present invention by manual operation.
3. Apparatus
(1) GC/MS: Trace GC, Polaris Q (ThermoFisher Scientific Corporation)

Ionization method EI, ion source temperature: 200° C., interface temperature: 280° C., Scan range (m/z): 50-450
(2) Sample introduction method: PTV splitless (ATAS GL OPTICS) injection port temperature: initial temperature 40° C., rate of temperature increase 16° C./second, final temperature 280° C. (5 minutes)
(3) Analysis column: InertCap 5MS, 0.25 mmID×30M, df=0.25 μm (GLS Corporation)
(4) GC oven temperature program: 40° C. (3 minutes)-20° C./minute-280° C. (10 minutes)
4. Results and Consideration The base peak m/z95 and the molecular ion peak M+168 were detected and confirmed to be 2-MIB and the base peak m/z112 and m+182 was detected and confirmed to be geosmin in the mass spectra (FIG. 32, FIG. 35) shown below FIGS. 30, 31 and FIGS. 33, 34.

Figure 30:
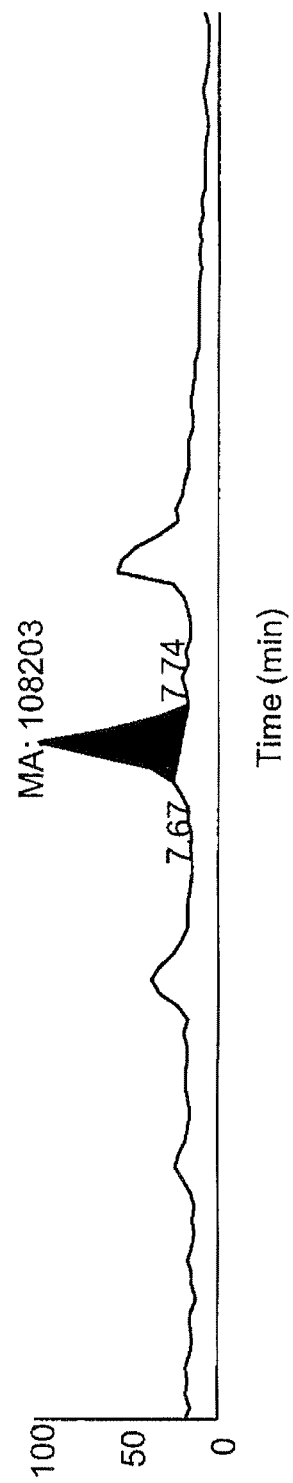
FIG. 30 is a chromatogram in an example of the present invention.
Figure 31:
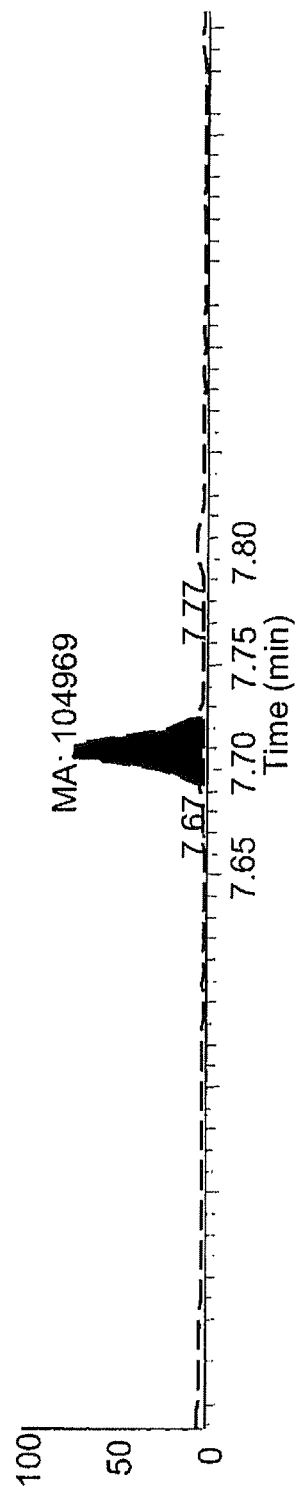
FIG. 31 is a chromatogram in an example of the present invention.
Figure 32:
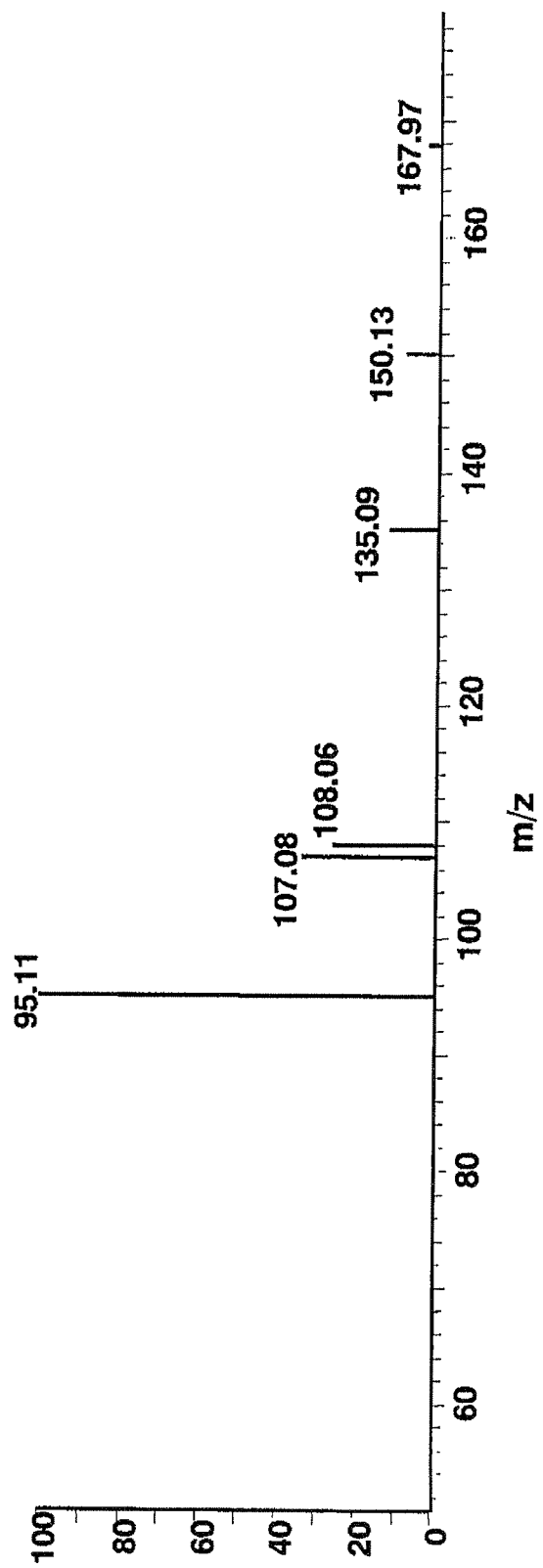
FIG. 32 is a chromatogram in an example of the present invention.
Figure 33:
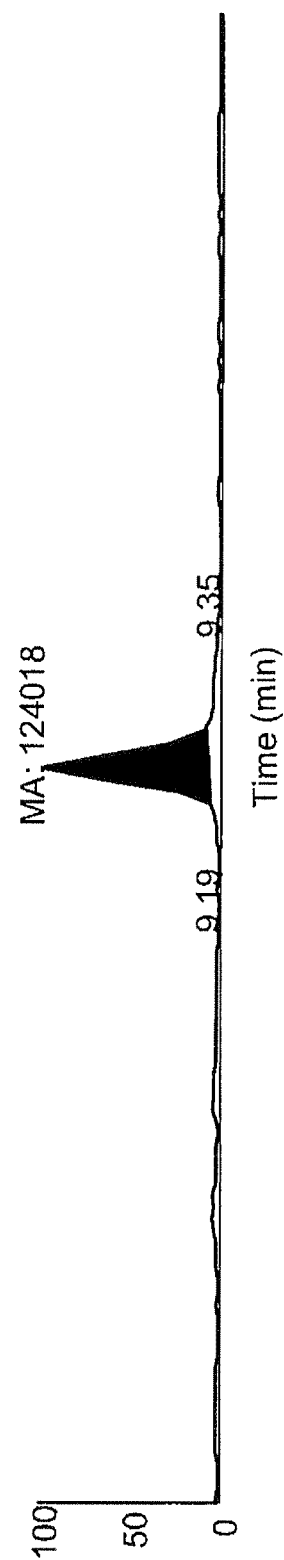
FIG. 33 is a chromatogram in an example of the present invention.
Figure 34:
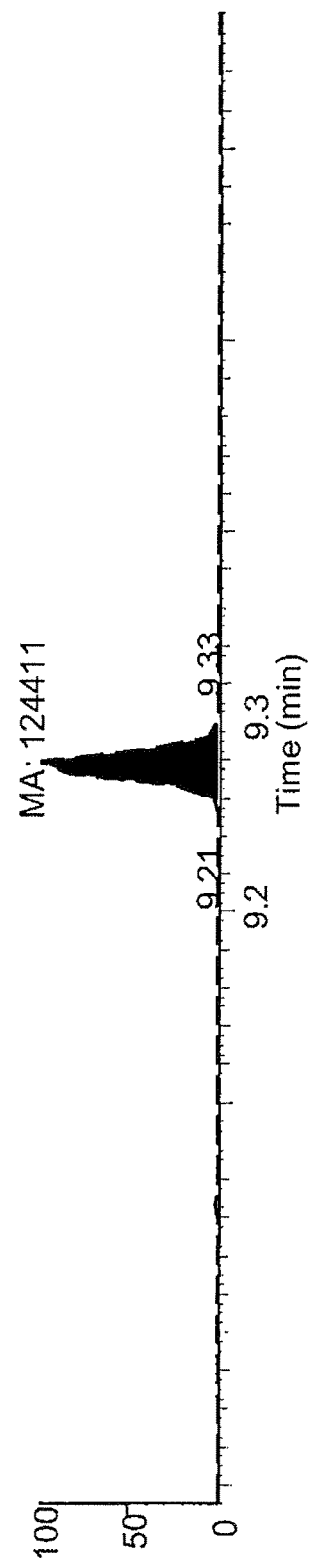
FIG. 34 is a chromatogram in an example of the present invention.
Figure 35:
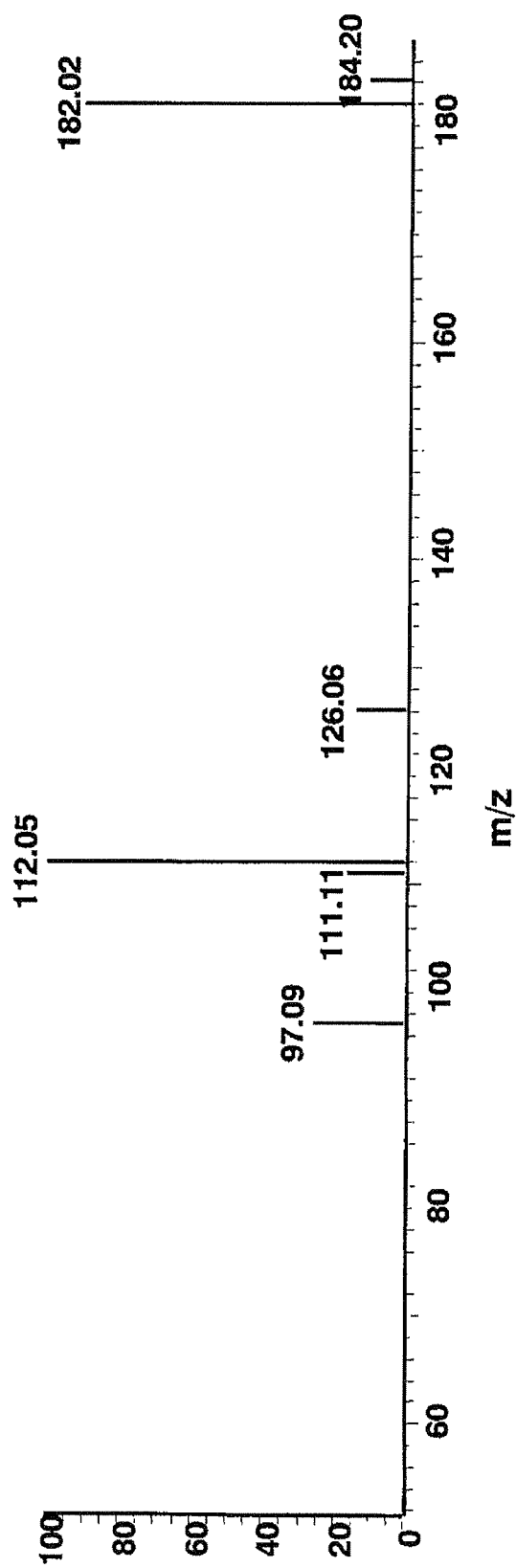
FIG. 35 is a chromatogram in an example of the present invention.

FIG. 30 and FIG. 33 are chromatograms for the case where 100 mL of the sample aqueous solution was flowed through the silica monolith type solid phase extractant and the total volume of the adsorption components was introduced by PTV splitless injection method and FIG. 31 and FIG. 34 are chromatograms for the case where 1 μL of the sample for confirming recovery ratio (1 ng/μL of 2-MIB and geosmin) was injected. FIG. 32 and FIG. 35 are mass spectra of 2-MIB and geosmin, respectively.

In FIGS. 30 and 31, FIGS. 33 and 34, the chromatogram peak area values at the upper and lower regions, which were daubed black, showed good agreement. This shows that the monolith adsorbent of the present invention has a high absorptivity for the mold odor components.

In addition, the peaks in good shape show that PTV splitless injection technique is available as thermal desorption sample introduction technique of the mold odor components which are adsorbed by the monolith adsorbent of the present invention.

EXAMPLE 13

Comparison with SBSE 5 ng of the following standard sample was added to the monolith adsorbent of the present invention and 20 mL of 15% NaCl aqueous solution and adsorbed with the monolith adsorbent and PDMS based SBSE. They were stirred in a constant temperature shaking water tank at 60° C., 90 rpm for 30 minutes.

The monolith adsorbent was extracted with dichloromethane, SBSE with acetonitrile each 200 μL in volume and measured.

Figure 38:
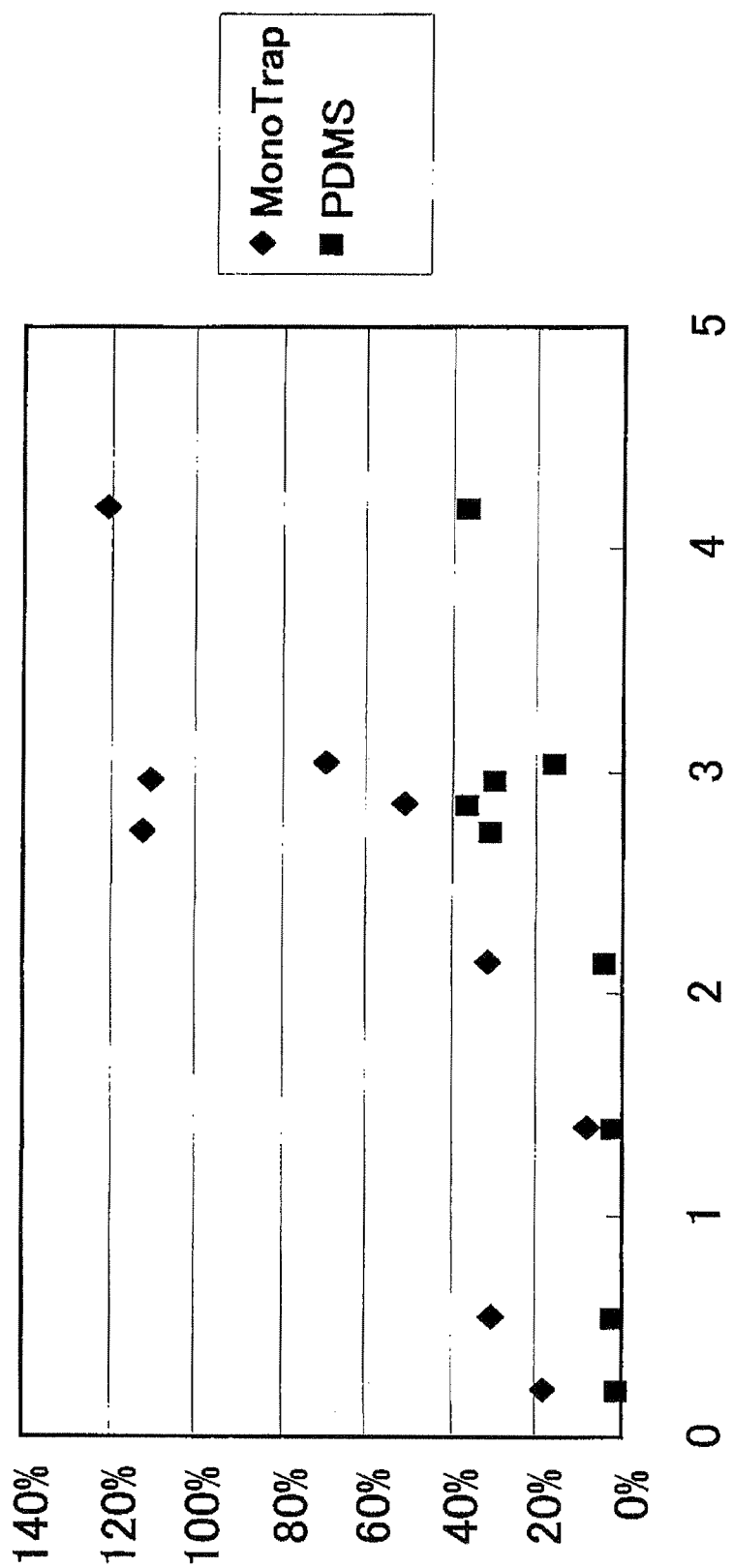
FIG. 38 is a graph comparing the recovery ratio between the present invention and a comparative article.

The absolute recovery was indicated with water octanol coefficient (LogP) of the sample as the horizontal axis (FIG. 38).

As sample has a lower LogP value, it is more hydrophilic, and recovery from the water becomes very difficult. The monolith adsorbent, however, generally attains higher recovery ratio than SBSE even for such samples. That is, recovery ratio of not less than 19% was attained even for the substances having water octanol coefficient of not more than 1 (methylpyrazine, 2,6-dimethylpyrazine).

(Water Octanol Coefficient:Sample)
0.21:Methylpyrazine
0.54:2,6-Dimethylpyrazine
1.39:Coumarin
2.14:Indole
2.74:Cineol
2.85:Orange clystal
2.97:Linalool
3.05:Caprylic acid
4.20:Limonene

EXAMPLE 14

Relation Between Adsorption Time and Recovery Ratio (for Gaseous Sample)

A standard gas sample (described in the drawing with the boiling point) was added to an airtightly stoppered vial (volume 40 mL) in a concentration in the gas of 125 ppb and allowed to adsorb (60° C.) with the monolith adsorbent (in the form of a disk).

Figure 39:
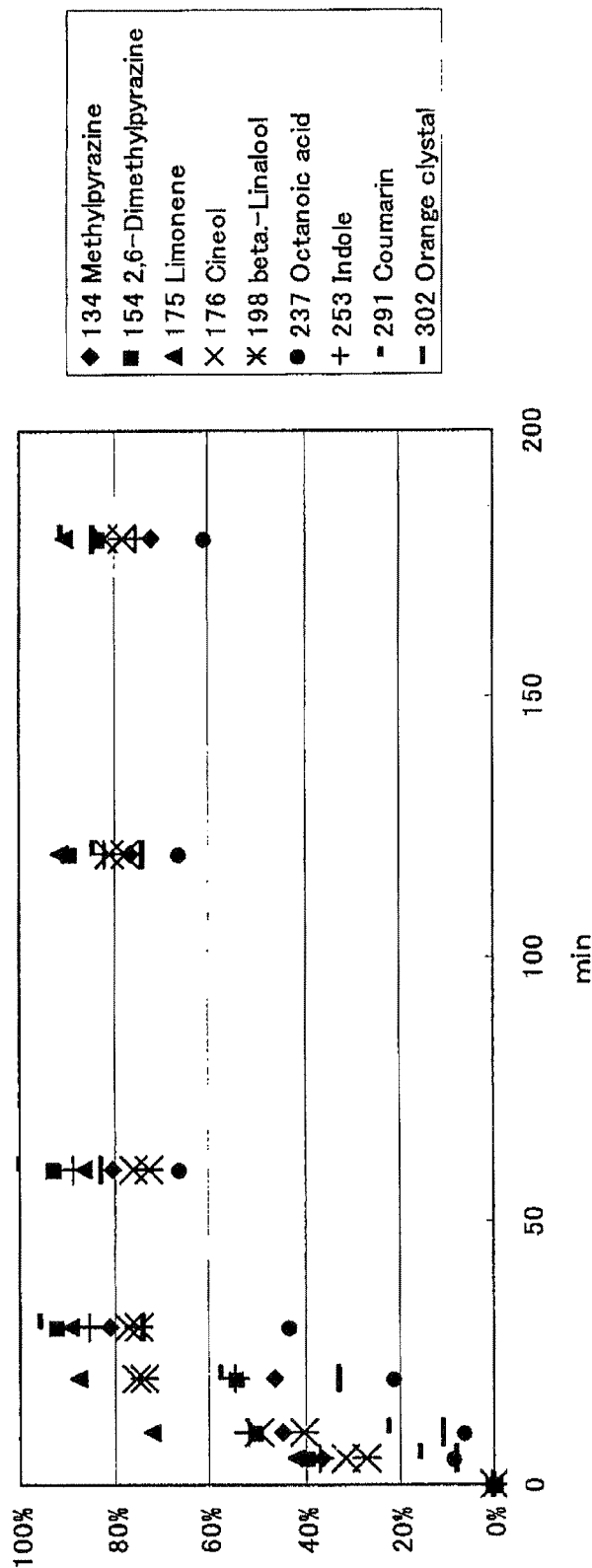
FIG. 39 illustrates the relation between the adsorption ratio and adsorption time in an example of the present invention.

The relation between the adsorption ratio and the retention time is shown in FIG. 39. In order to attain secured adsorption, adsorption time of around 30 to 60 minutes is necessary but sufficient recovery is enabled even for a shorter time depending on a sample.

Adsorption and adsorption of the liquid phase by PDMS and extraction from a liquid due to phase equilibrium require long time but the monolith adsorbent readily enables short time adsorption since in the monolith adsorbent the sample goes into the space among the adjacent ODS groups bonded to the surface area of the silica backbone, which has a large effect on the adsorption.

EXAMPLE 15

Relation Between Temperature and Adsorption Ratio (for Gaseous Sample)

The adsorption ratios for the cases where temperature at the time of adsorption is 30° C. and 60° C. in the above EXAMPLE 14 were compared (adsorption time, 30 minutes).

Figure 40:
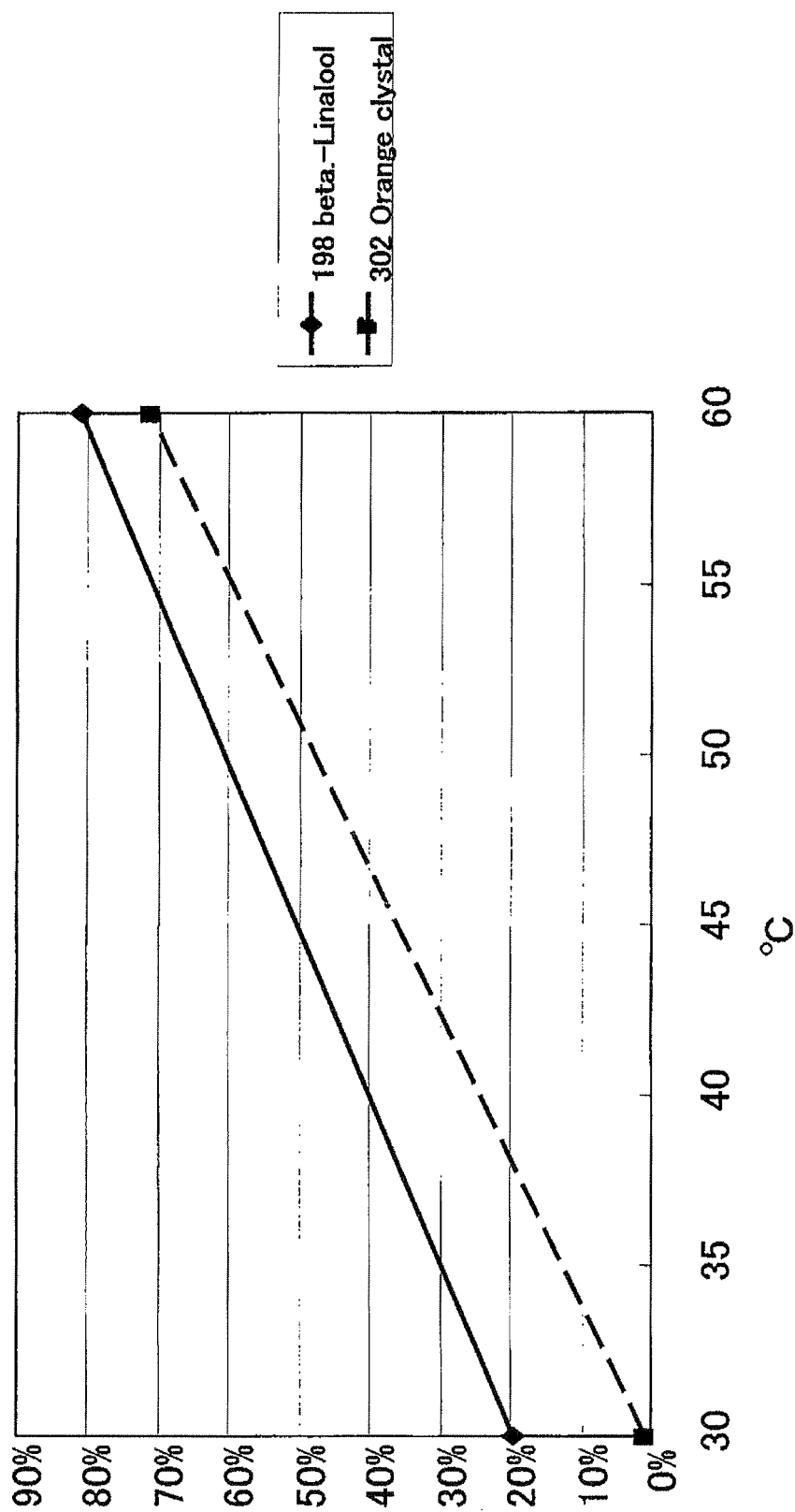
FIG. 40 is a graph comparing a temperature and recovery ratio in an example of the present invention.

The diffusivity of the gas depends on the temperature, and therefore, the adsorption time can be shortened by warming. The results of the experiment for linalool and orange crystal having low sample activity are shown in FIG. 40.

EXAMPLE 16

Salting-Out

Figure 41:
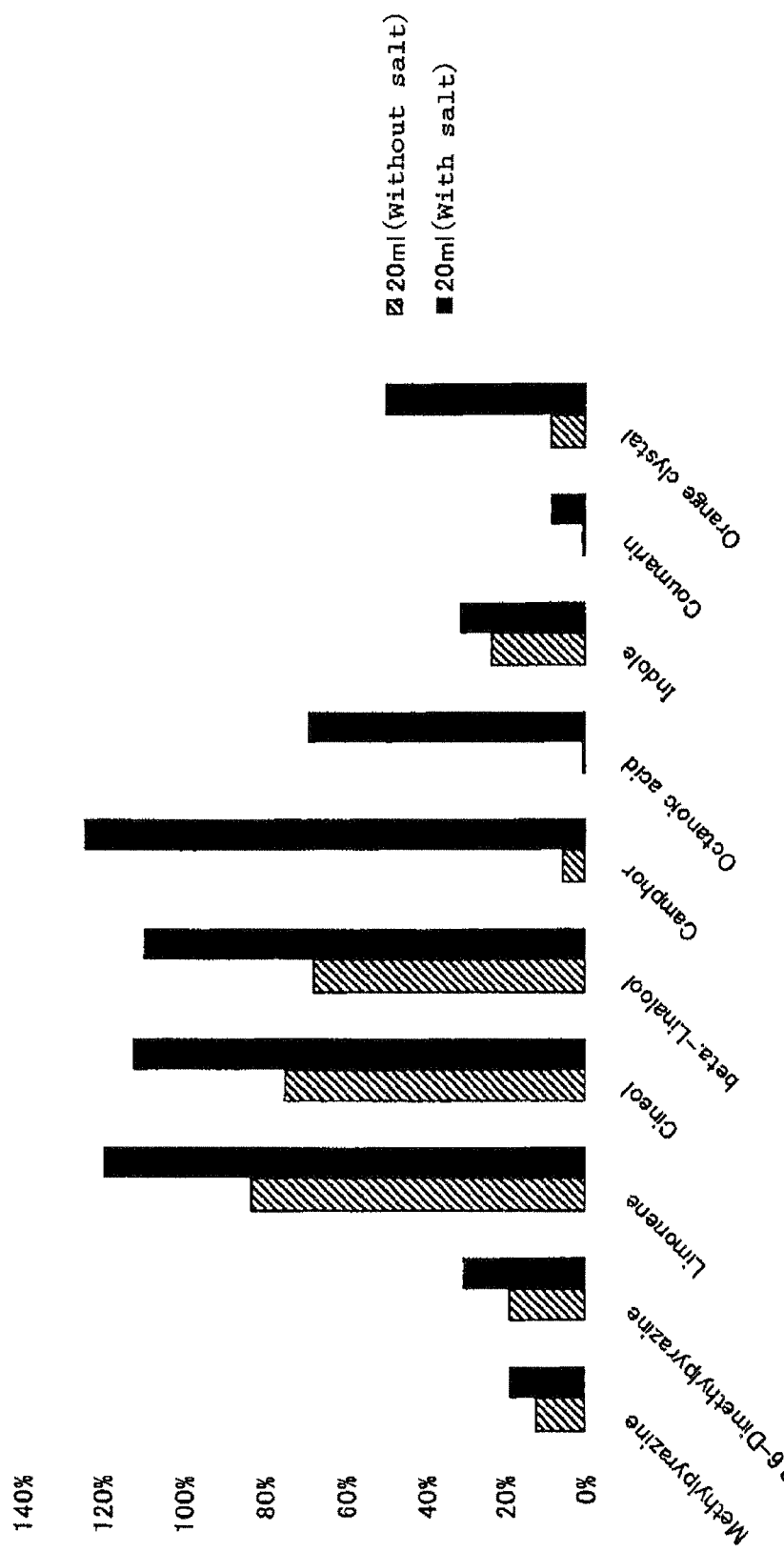
FIG. 41 is a graph comparing the effect of salting-out in an example of the present invention.

25 μL of a standard sample (200 μg/mL) was added to 20 mL of 15% NaCl aqueous solution and the solution was adsorbed with one piece of disk-shaped monolith adsorbent. The solution was stirred at 60° C., 90 rpm in a constant temperature shaking water tank for 30 minutes. As a result, adsorption ratio was increased by salting out effect totally as shown in FIG. 41.

EXAMPLE 17

Relation Between Adsorption Time and Adsorption Ratio (for Liquid Sample).

25 μL of a standard sample (200 μg/mL) was added to 20 mL of 15% NaCl aqueous solution and the solution was adsorbed with one piece of disk-shaped monolith adsorbent. The solution was stirred at 60° C., 90 rpm in a constant temperature shaking water tank. The headspace was also warmed at 60° C. and left untouched.

Figure 42:
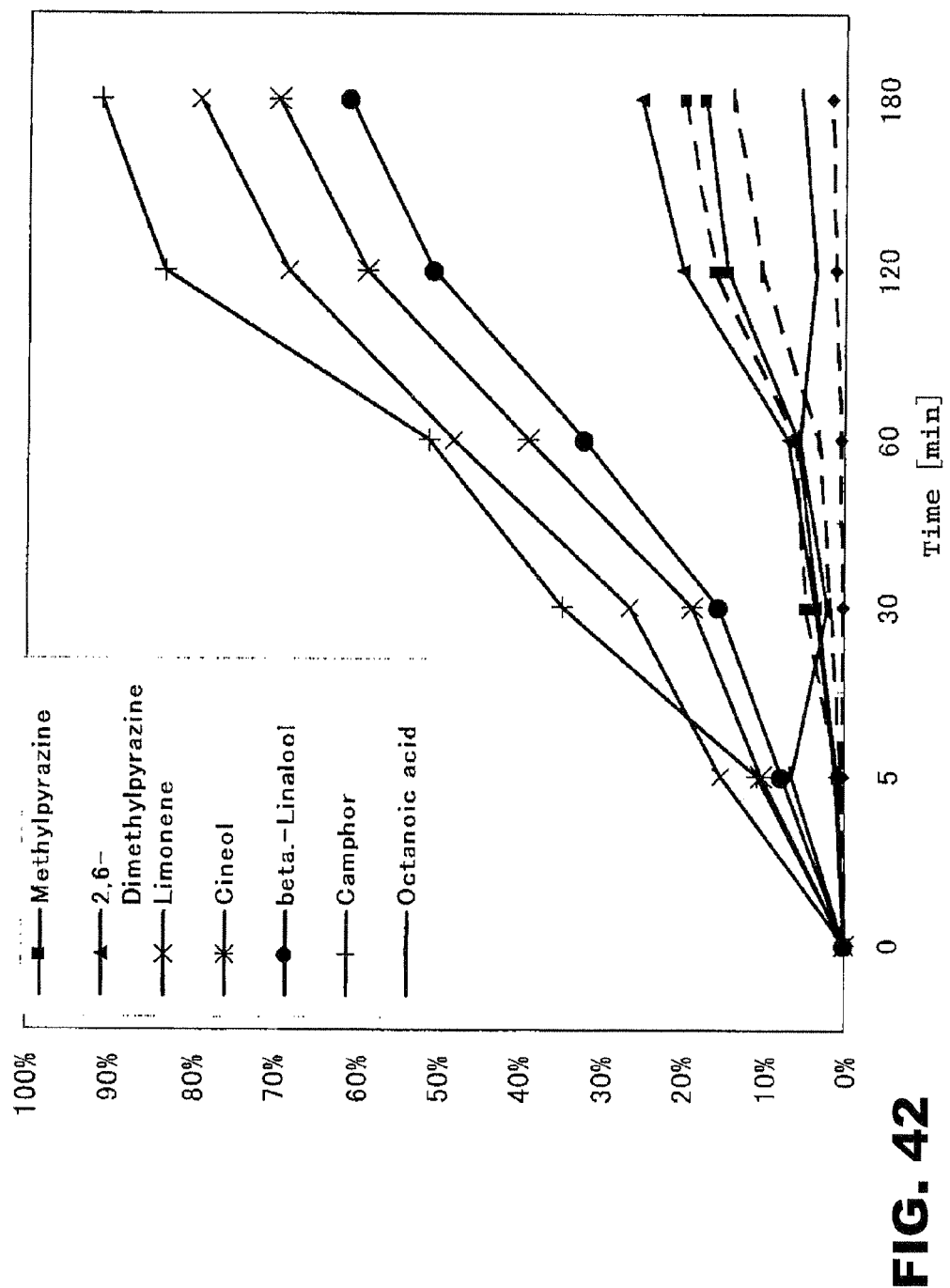
FIG. 42 illustrates the comparison of the equilibrium in an example of the present invention.
Figure 43:
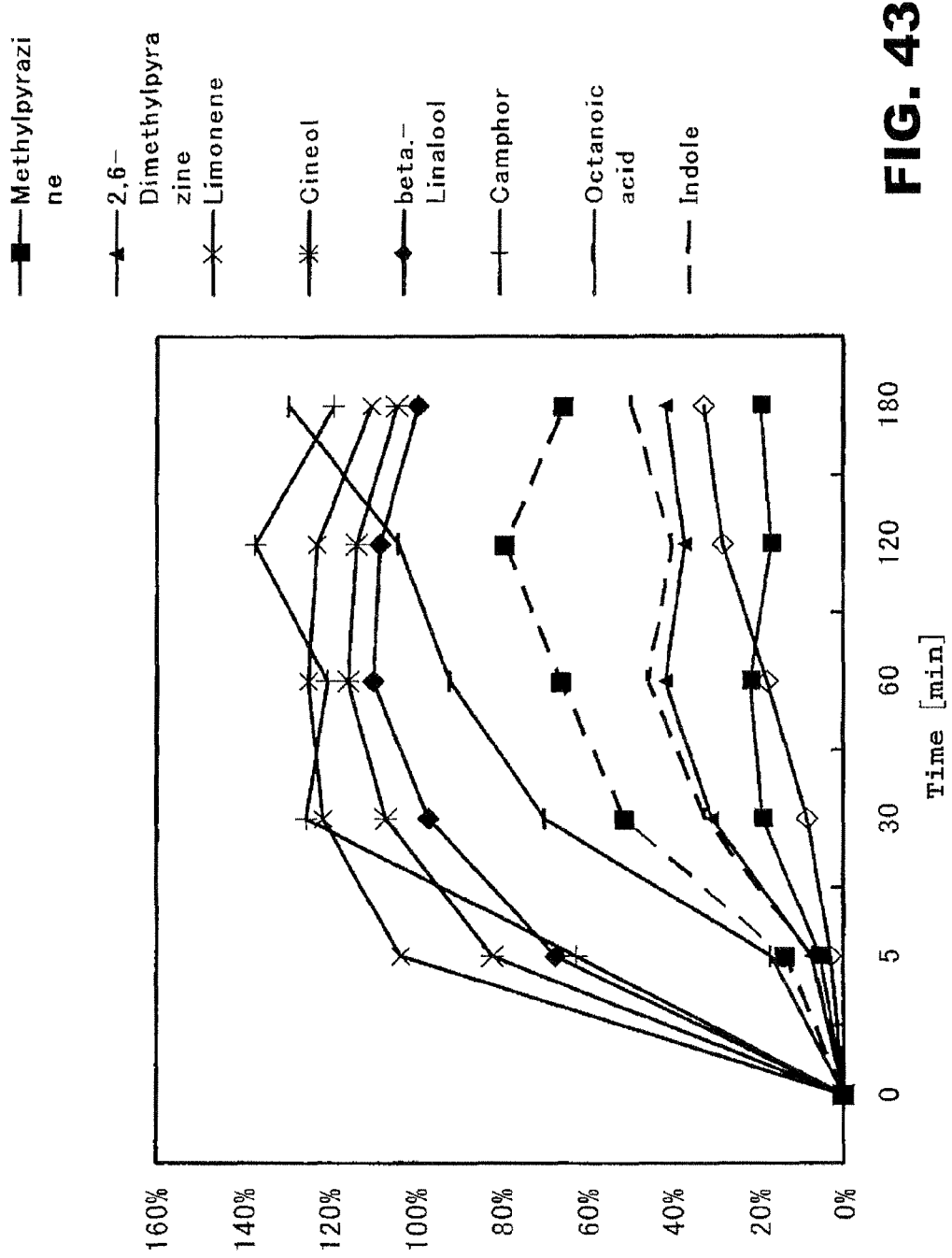
FIG. 43 illustrates the comparison of the equilibrium in an example of the present invention.

In the case of headspace method, time to reach the equilibrium by diffusion is needed (FIG. 42). In the case of performing stirring, the system reaches the equilibrium for around 30 minutes (FIG. 43).

However, in the case of acidic sample octanoic acid, it takes around 60 minutes.

EXAMPLE 18

Relation Between pH Adjustment and Recovery Ratio (Liquid Sample)

25 μL of a standard sample (200 μg/mL) was added to 20 mL of 15% NaCl aqueous solution (adjusted to pH 2 with 1M monophosphate) and the solution was adsorbed with one piece of disk-shaped monolith adsorbent. The solution was stirred at 60° C., 90 rpm in a constant temperature shaking water tank for 30 minutes. The headspace (HS) was also warmed at 60° C. and left untouched for 30 minutes.

Figure 44:
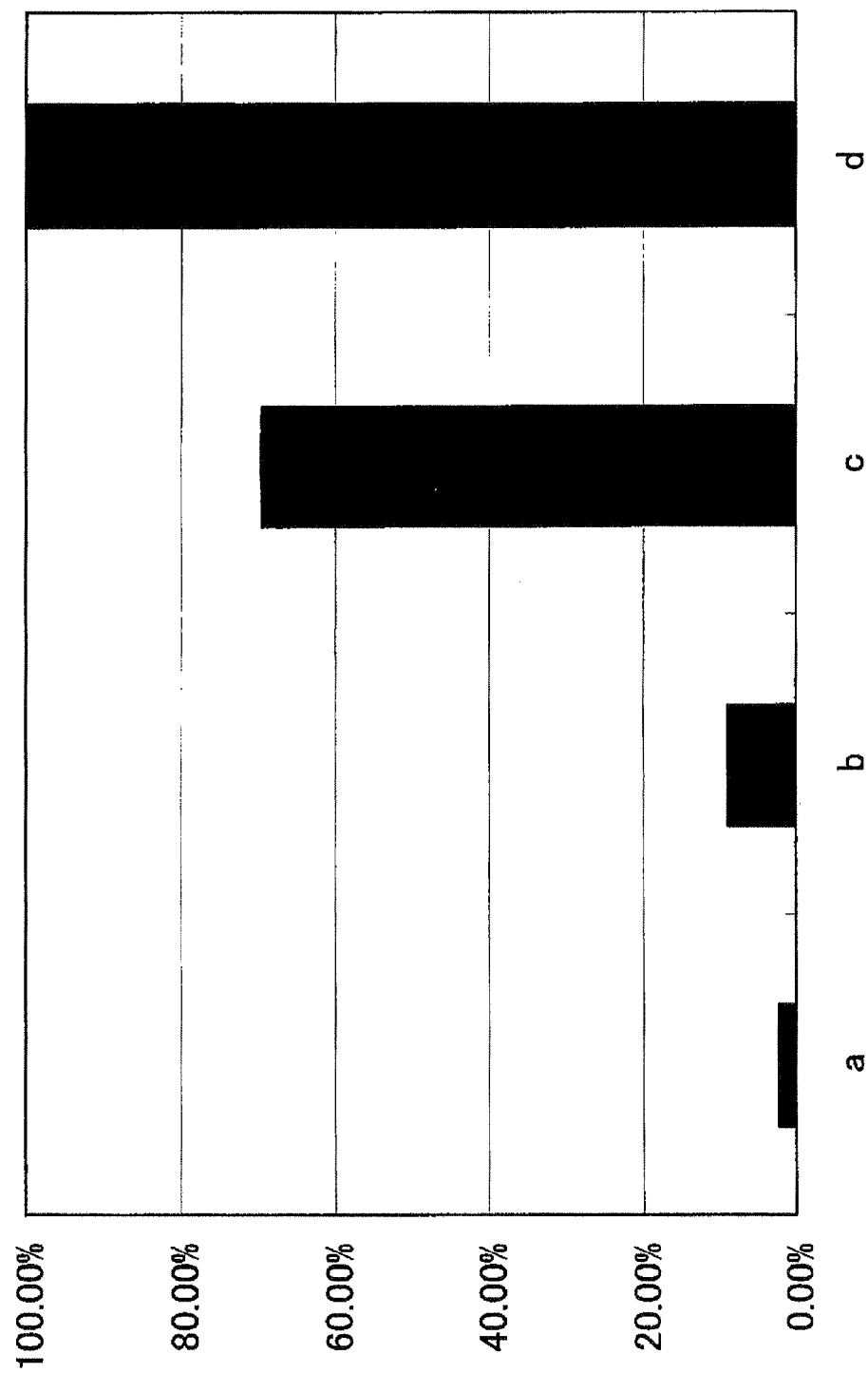
FIG. 44 illustrates the relation relating to pH in an example of the present invention.

The effect of the presence/absence of the pH adjustment of the sample (with octanoic acid) is shown for HS and as the result of stirring in FIG. 44.

a: HS
b: pH adjusted HS
c: stirring
d: pH adjusted stirring

It can be understood that adsorption ratio was improved by controlling pH of the aqueous sample. Salting-out is effective for the adsorption of the aqueous sample but further improvement in the adsorption ratio is enabled by further controlling pH of the aqueous sample.

The adsorption/extraction efficiency greatly depends on the characteristics of the sample and the influence of the matrix in the case of a liquid sample and therefore it becomes effective for improving adsorption ratio to use the techniques such as salting-out and pH adjustment together.

EXAMPLE 19

Relation Between Supersonic Wave Irradiation and Adsorption Ratio

A standard sample was added to an airtightly stoppered vial (volume 40 mL) in terms of a concentration in the gas of 125 ppb and allowed to adsorb (60° C.) with the disk-shaped monolith adsorbent. Measurement was performed while the time for performing ultrasonic wave treatment at the time of solvent extraction was changed.

Figure 45:
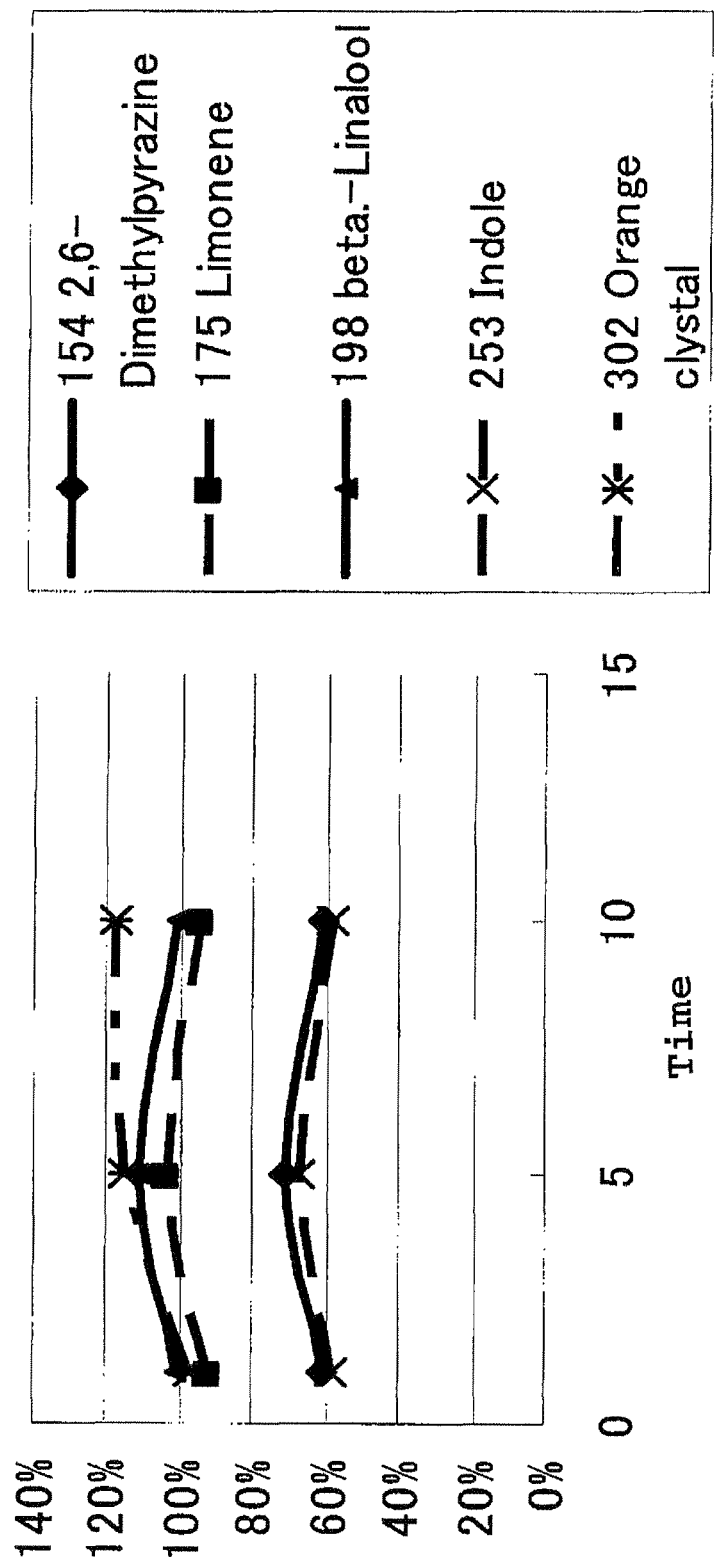
FIG. 45 is a graph comparing the effect of radiation of supersonic wave in an example of the present invention.

The change in the adsorption ratio when using 500 μL of dichloromethane depending on the time for irradiating a supersonic wave is shown in FIG. 45. It can be understood that sufficient adsorption ratio is obtained by irradiating a supersonic wave for around one minute.

EXAMPLE 20

Extractant

A standard sample was added to an airtightly stoppered vial (volume 40 mL) in terms of a concentration in the gas of 100 ppb and allowed to adsorb (60° C.) with the disk-shaped monolith adsorbent and then extracted with 500 μL of a solvent.

Figure 46:
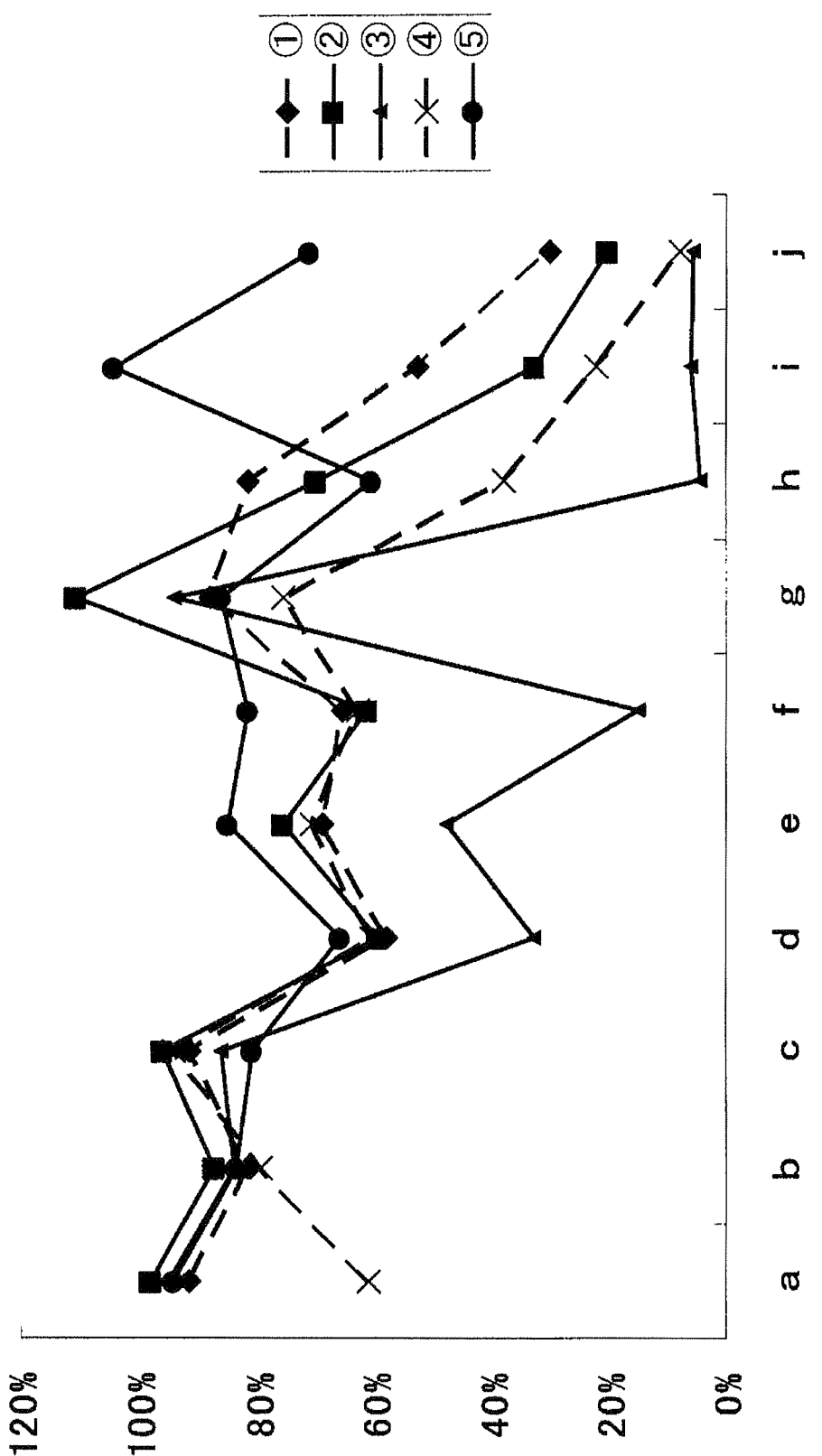
FIG. 46 illustrates the relation relating to solvents in an example of the present invention.

The solvent to use at the time of extraction is selected in accordance with the target sample. Commonly used acetone (①in FIG. 46), diethyl ether (② in FIG. 46), C6 (③ in FIG. 46), methanol (④ in FIG. 46), dichloromethane (⑤ in FIG. 46), ethanol, hexane (⑤ in FIG. 46) can be used. In this experiment, dichloromethane could extract in a good balance.

a: Limonene, b: Cineol, c: beta-Linalool, d: Methylpyrazine, e: 2,6-Dimethylpyrazine, f: Indole, g: Camphor, h: Octanoic acid, i: Coumarin, j: Orange clystal (FIG. 46)

EXAMPLE 21

In the case of a monolith structure body for removing matrix components 43 or the like (monolith pre-filter 41), a reagent which can remove or retain the object components is allowed to react with the surface of the monolith structure body or to be contained in the monolith in itself. Typical examples include ion exchange phase (SAX, SCX, etc.), special bonding phase (PBA, etc.), polar phase (S1, FL, etc.), nonpolar phase (SDB, C18, etc.), normal phase adsorption (activated carbon, graphite carbon, ion exchange system, C1, CN).

Figure 28:
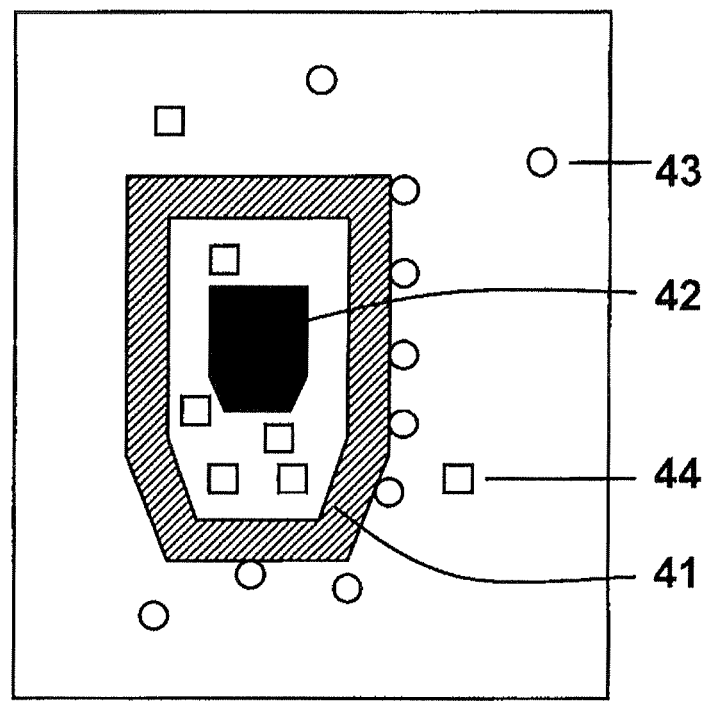
FIG. 28 is a schematic view illustrating an example of the present invention.

These can be naturally contained in monolith adsorbent 42 or the monolith adsorbent 42 can be modified thereby. When more selective retaining is desired, for example, the monolith pre-filter 41 is allowed to contain activated carbon and to remain hydrophilic without being treated with ODS, and thereby selective retaining with the inner monolith adsorbent 42 is enabled (FIG. 28).

EXAMPLE 22

The monolith pre-filter 41 is allowed to remain hydrophilic without being treated with ODS while allowing the inner monolith adsorbent 42 to be hydrophobic. For organophosphate pesticides, moisture contained in the pesticides is adsorbed by the outer pre-filter and the hydrophobic pesticidal components (malathion, fenitrothion, MEP, trichlorfon, DDVP, dichlorvos, methidathion, acephate, isoxathion, etc. designated as 44) can be adsorbed by the inner part.

Quick use of antidote PAM is necessary in determining the treatment policy for the poisoning by an organophosphate pesticides. It is important to establish the method for rapidly analyzing the organophosphate pesticide in the vomit or the other samples from the living body. Use of the present invention shortens the time for adsorption and extraction and therefore it is considerably useful for the purpose.

In addition, since the organophosphate pesticide is volatile, concentration of the target component obtained by solvent extraction requires careful attention. Since the present invention adsorbs the target component in the closed system and enables to analyze the target component as it is by GC and LC, the above problem can be annihilated.

EXAMPLE 23

Samples having a water octanol coefficient (LogP) value as low as 1 or less (i.e., having hydrophilicity), which is an index of hydrophilicity/hydrophobicity, are difficult to extract from water.

For example, acetic acid has LogP of 0.09, and the extraction methods thereof include an approach to make the solution acidic and means such as salting-out but these are laborsome and difficult to perform.

In this way, a hydrophobic surface of the monolith adsorbent repels moisture for hydrophilic substances such as fatty acids (in particular, acetic acid, propionic acid, butyric acid) in water, apertures (mesopores) inside the silica backbone do not participate in the adsorption and thus the adsorption becomes difficult.

Therefore by making the surface of the monolith adsorbent hydrophilic, compatibility between the sample and the adsorbing material is improved, and the adsorption of the target component becomes easy as well. In order to make the surface hydrophilic, the surface of the adsorbing material is subjected to acid treatment or treatment with a reaction reagent such as alkoxysilane having a diol group.

Figure 47:
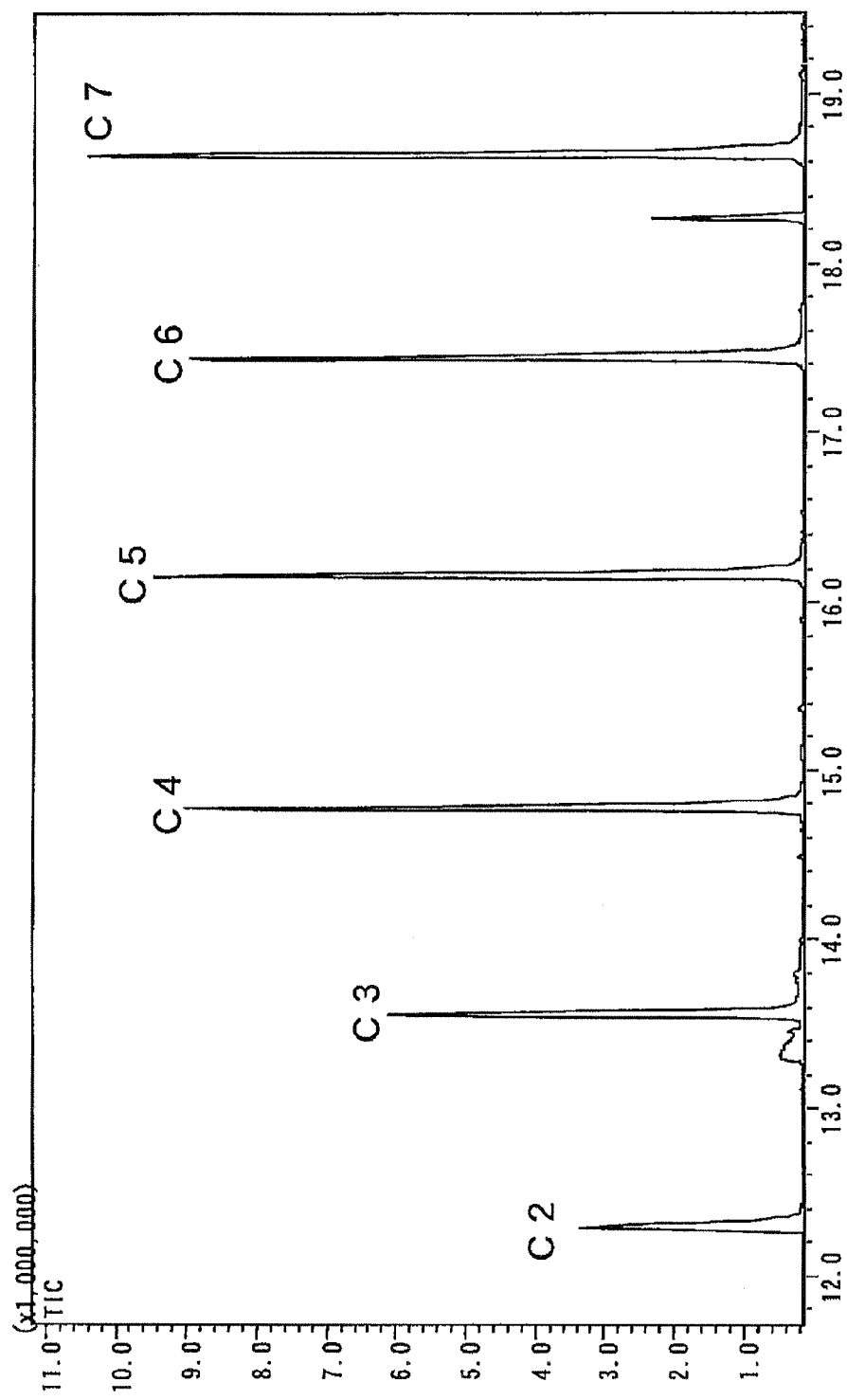
FIG. 47 illustrates the performance test of the adsorbent in an example of the present invention.

In order to adsorb fatty acids (following C2 to C7) in water, the adsorbing material was made hydrophilic by using a reaction reagent and the adsorbing material was impregnated in a sample solution in this example. The above monolith adsorbent was heated to 60° C. and purge gas was blown thereto to remove moisture and then solvent extraction with diethyl ether was performed. (FIG. 47)

Figure 48:
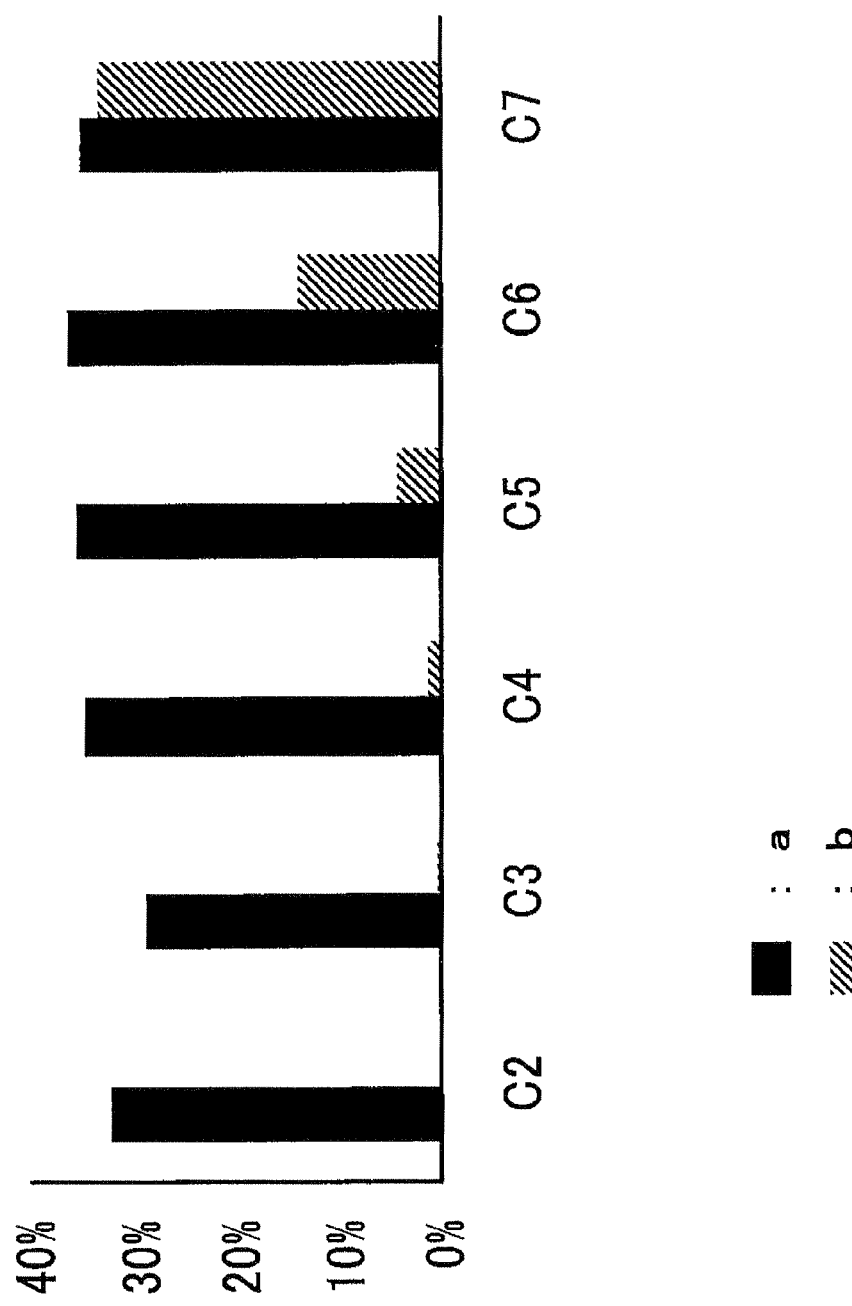
FIG. 48 illustrates the comparison of the adsorption by the adsorbent in an example of the present invention.
Figure 49:
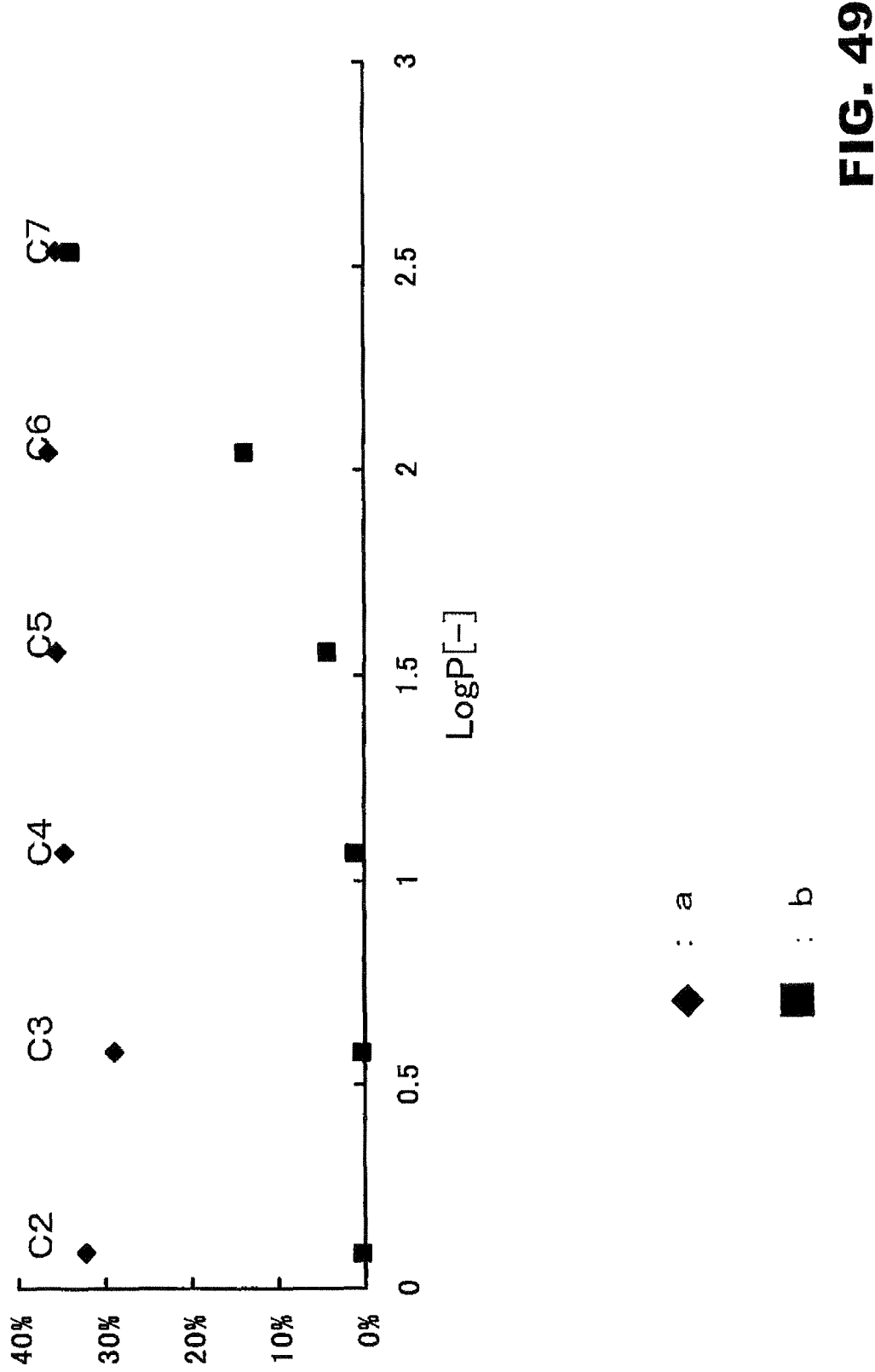
FIG. 49 illustrates the comparison of the adsorption by the adsorbent in an example of the present invention.

C2: Acetic acid
C3: Propionic acid
C4: Butyric acid
C5: Valerie acid
C6: Caproic acid
C7: Heptyric acid The comparison in the adsorbing materials having hydrophilic surface (a)/hydrophobic surface (b) in each sample mentioned above is shown in FIG. 48. In addition, comparison in which water octanol coefficient (LogP) is used as a horizontal axis is shown in FIG. 49. It can be understood from these results that the present invention is useful for the hydrophilic samples having low water octanol coefficient.

INDUSTRIAL APPLICABILITY

According to the present invention, in spite of using a stationary phase having the same volume as in SPME and SBSE, the thickness of the stationary phase itself is reduced while the surface area is increased by using a monolith structure body, and as a result, adsorbing (to reach the equilibrium) and extracting (desorbing) the components can be performed in a short time.

In addition, the effect by the adsorbing material exposed on the surface area of the monolith structure body and the effect by the hydrophobic or hydrophilic compound such as ODS (octadecylsilane) and SDB (styrene divinylbenzene copolymer) or diols which have been reacted with the surface of the monolith structure body are synergistic and thus the adsorption ability can be optionally enhanced by further performing surface treatment by applying a resin (PDMS (polydimethylsiloxane), PEG (polyethylene glycol), etc.) to the whole monolith adsorbent.

Besides, the monolith structure body has continuous pore structures and a number of mesopores and therefore has a large surface area. Accordingly, the contact area of the sample components in the target solution and the adsorbing material and the alkoxysilane based samples such as ODS is large, which enhances the adsorption ability.

The synergistic effects of the surface area, adsorbing materials, hydrophobic/hydrophilic compounds, reagents and so on as mentioned above enable to improve the adsorption of the sample.

When a sample compound held by PDMS or the like is eluted, release proceeds in accordance with phase equilibrium and therefore the conventional methods with a small surface area are disadvantageous. In contrast, since the present method uses a monolith adsorbent having a large surface area, the contact area with a gas or a solvent for desorption is large at the time of elution and release of an extremely small amount of gas or a solute component in the solvent is enabled.

In addition, increase in the surface area and improvement in the ability of adsorption mean the downsizing of monolith adsorbent in itself and have significance particularly in GC and LC analysis. For example, if the adsorbent of the present invention can be accommodated in a current GC auto-sampler vial, release of the components can be performed with a small amount of a solvent, and an autoanalysis with the auto-sampler is enabled in a state as it is, and thus concentration and analysis are enabled extremely readily and inexpensively.

When environmental water is concentrated and analyzed, there is a case that a matrix component coexisting in the environmental water may interfere with the analysis of the target sample. Currently, the interfering components are removed by pre-filtration and the like before concentration, this step is often time-consuming and troublesome.

In contrast, the method of the present invention enables the removal of the interfering components and selective adsorption and retention of the target sample alone at a time. The matrix is removed by a monolith structure body of the covering part and further the target sample alone is selectively adsorbed in the inner adsorption monolith material.

Figure 29:
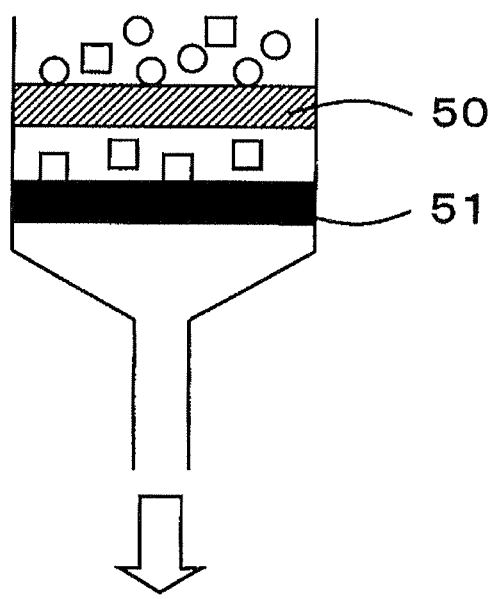
FIG. 29 is a schematic view illustrating an example of the present invention.

In addition, the same effect can be obtained when a disk-shaped matrix removal mechanism 50 (which corresponds to the above-mentioned covering part) is provided in the container so that monolith adsorbent 51 may be in a close contact with the container (FIG. 29).

Further effect in the aspect of adsorbed amount, adsorption time and readiness in adsorption (several times of pumping) can be obtained by precisely sending the sample solution to the matter monolith adsorbent of the present invention. Recovering effect with a little solvent is resulted by sending the solvent for extraction of the target components in the same way, and as a result, analysis in high concentration is enabled.

In addition, an effect of reducing the extraction time is resulted in the heat extraction. These effects result in sharp peaks in the chromatogram and suppress thermal load of the target components, and also lead to the effect that sufficient adsorbed amount can be obtained without being affected by the existence of the matrix.

In addition, according to the monolith adsorbent of the present invention, the sample which has been adsorbed in the monolith adsorbent can be eluted by a solvent or heat and can be introduced into the analyzer just as it is. That is, the laborious steps of eluting the sample in a container and then transferring the sample to the injection port as performed in the conventional method can be omitted, and that the present method has effects that the desorption is possible with only a little solvent and the thermal desorption can be facilitated.

The sample can be surely held in the apparatus and method of the present invention when a large amount of the sample in a low concentration is made to flow without outflow (breakthrough, etc.) of the target sample from the adsorbing material. The structure body can surely retain the sample with least possibility of being damaged.

In the present invention, the sample as either a liquid or a gas can be handled, and a liquid sample can be applied to pumping, impregnation, stirring in the solution, headspace, dynamic headspace, a stirrer or the like and a gaseous sample can be applied both to an active sampler and a passive sampler.

What is claimed is:
1. A monolith adsorbent comprising:
a monolith structure body having continuous and interconnected through-holes in the form of a three-dimensional network; and
a particulate adsorbing material contained in the monolith structure body such that the particulate adsorbing material is at least partially exposed on a surface of and at least partially embedded in the monolith structure body in a random manner, and the particulate adsorbing material is fixed to the monolith structure body by the monolith structure body itself, and additionally comprising a chemical substance applied or chemically bonded to the monolith structure body, wherein the adsorbing material comprises at least one material selected from the group consisting of activated carbon, graphite carbon, carbon nanotube, fullerene, molecular sieve, zeolite, diatomaceous earth, divinylbenzene copolymers, molecular sieve carbon, activated alumina and magnesium silicate.
2. The monolith adsorbent according to claim 1, wherein the chemical substance is a hydrophobic chemical substance chemically bonded to the surface of the monolith structure body.
3. The monolith adsorbent according to claim 1, wherein the chemical substance is a hydrophilic chemical substance chemically bonded to the surface of the monolith structure body.
4. The monolith adsorbent according to claim 1, wherein a resin is applied or chemically bonded to the surface of the monolith structure body.
5. The monolith adsorbent according to claim 2, wherein a resin is further applied or chemically bonded to the monolith structure body which has been surface-treated with the hydrophobic chemical substance.
6. The monolith adsorbent according to claim 2, wherein the hydrophobic chemical substance comprises at least one compound having a functional group selected from the group consisting of an octadecyl group, a methyl group, an ethyl group, an octyl group, a cyclohexyl group, a vinyl group, and a phenyl group.
7. The monolith adsorbent according to claim 3, wherein a resin is further applied or chemically bonded to the monolith structure body which has been surface-treated with the hydrophilic chemical substance.
8. The monolith adsorbent according to claim 3, wherein the hydrophilic chemical substance comprises at least one compound having a functional group selected from the group consisting of a diol group, a cyanopropyl group, a carboxyethyl group, a propylsulfonyl group, a benzenesulfonylpropyl group, an aminopropyl group, an ethylenediamine N-propyl group, a trimethylaminopropyl group, and a polyamide group.
9. The monolith adsorbent according to claim 4, wherein the resin comprises at least one compound selected from the group consisting of a siloxane backbone resin, a hydrophilicity resin, and a hydrophobicity resin.
10. The monolith adsorbent according to claim 5, wherein the hydrophobic chemical substance comprises at least one compound having a functional group selected from the group consisting of an octadecyl group, a methyl group, an ethyl group, an octyl group, a cyclohexyl group, a vinyl group, and a phenyl group.
11. The monolith adsorbent according to claim 5, wherein the resin comprises at least one compound selected from the group consisting of a siloxane backbone resin, a hydrophilicity resin, and a hydrophobicity resin.

12. The monolith adsorbent according to claim 7, wherein the hydrophilic chemical substance comprises at least one compound having a functional group selected from the group consisting of a diol group, a cyanopropyl group, a carboxyethyl group, a propylsulfonyl group, a benzenesulfonylpropyl group, an aminopropyl group, an ethylenediamine N-propyl group, a trimethylaminopropyl group, and a polyamide group.

13. The monolith adsorbent according to claim 7, wherein the resin comprises at least one compound selected from the group consisting of a siloxane backbone resin, a hydrophilicity resin, and a hydrophobicity resin.

14. The monolith adsorbent according to claim 9, wherein the siloxane backbone resin comprises at least one compound selected from the group consisting of polydimethylsiloxane, silphenylene siloxane, diphenylsiloxane, cyanopropylphenylsiloxane and cyanopropylsiloxane.

15. The monolith adsorbent according to claim 9, wherein the hydrophilicity resin comprises at least one compound selected from the group consisting of polyethylene glycol, polyethylene glycol terephthalate, polypropylene, glycol, carbowax, polyacrylic acid and polyamine.

16. The monolith adsorbent according to claim 9, wherein the hydrophobicity resin comprises at least one compound selected from the group consisting of divinylbenzene copolymers, styrene copolymers and propylene copolymers.

17. The monolith adsorbent according to claim 11, wherein the siloxane backbone resin comprises at least one compound selected from the group consisting of polydimethylsiloxane, silphenylene siloxane, diphenylsiloxane, cyanopropylphenylsiloxane and cyanopropylsiloxane.

18. The monolith adsorbent according to claim 11, wherein the hydrophilicity resin comprises at least one compound selected from the group consisting of polyethylene glycol, polyethylene glycol terephthalate, polypropylene, glycol, carbowax, polyacrylic acid and polyamine.

19. The monolith adsorbent according to claim 11, wherein the hydrophobicity resin comprises at least one compound selected from the group consisting of divinylbenzene copolymers, styrene copolymers and propylene copolymers.

20. The monolith adsorbent according to claim 13, wherein the siloxane backbone resin comprises at least one compound selected from the group consisting of polydimethylsiloxane, silphenylene siloxane, diphenylsiloxane, cyanopropylphenylsiloxane and cyanopropylsiloxane.

21. The monolith adsorbent according to claim 13, wherein the hydrophilicity resin comprises at least one compound selected from the group consisting of polyethylene glycol, polyethylene glycol terephthalate, polypropylene, glycol, carbowax, polyacrylic acid and polyamine.

22. The monolith adsorbent according to claim 13, wherein the hydrophobicity resin comprises at least one compound selected from the group consisting of divinylbenzene copolymers, styrene copolymers and propylene copolymers.

23. An apparatus for adsorbing a sample comprising:
a filter having a monolith structure body and a monolith adsorbent in a housing accommodating a liquid or gaseous sample, wherein the monolith adsorbent is constructed by containing an adsorbing material in a second monolith structure body, wherein the adsorbing material exposed on the second monolith structure body, and the second monolith structure body is surface treatable.

24. The apparatus for adsorbing a sample according to claim 23, Wherein the filter is formed in the form of a container and the monolith adsorbent is provided in the container for adsorbing a target component.

25. The apparatus for adsorbing a sample according to claim 23, Wherein the monolith structure body of the filter has a through-pore which is formed larger than a through-pore of the monolith adsorbent.

26. The apparatus for adsorbing a sample according to claim 23, Wherein the monolith structure body of the filter have been reacted with a compound selected from the group consisting of a hydrophilic compound, a hydrophobic compound, and an ionic functional group.

27. An apparatus for adsorbing a sample comprising:
a monolith adsorbent disposed on a rotating stirrer, wherein the monolith adsorbent adsorbs a target component by rotating the stirrer, and wherein the monolith adsorbent is constructed by containing an adsorbing material in a monolith structure body, wherein the adsorbing material is exposable on the structure body, and the structure body is surface treatable.

28. An apparatus for adsorbing a sample comprising:
a monolith adsorbent attached in a closely contactable container, wherein the monolith adsorbent adsorb and extracts a target component, and wherein the monolith adsorbent is constructed by containing a particulate adsorbing material in a monolith structure body, and wherein the monolith structure body has continuous and interconnected through-holes in the form of a three-dimensional network, and wherein the adsorbing material comprises at least one material selected from the group consisting of activated carbon, graphite carbon, carbon nanotube, fullerene, molecular sieve, zeolite, diatomaceous earth, divinylbenzene copolymers, molecular sieve carbon, activated alumina and magnesium silicate, wherein the adsorbing material is at least partially embedded in the monolith structure body and at least partially exposed on the surface of the monolith structure body in a random manner, and the particulate adsorbing material is fixed to the monolith structure body by the monolith structure body itself, and the monolith structure body is surface treatable.

29. A method for adsorbing a sample comprising the steps of:
containing a monolith adsorbent in a container accommodating a liquid or gaseous sample; and impregnating the monolith adsorbent with the sample, wherein the monolith adsorbent is constructed by containing a particulate adsorbing material in a monolith structure body, and wherein the monolith structure body has continuous and interconnected through-holes in the form of a three-dimensional network, and wherein the adsorbing material comprises at least one material selected from the group consisting of activated carbon, graphite carbon, carbon nanotube, fullerene, molecular sieve, zeolite, diatomaceous earth, divinylbenzene copolymers, molecular sieve carbon, activated alumina and magnesium silicate, wherein the adsorbing material is at least partially embedded in the monolith structure body and at least partially exposed on the surface of the monolith structure body in a random manner, and the particulate adsorbing material is fixed to the monolith structure body by the monolith structure body itself, and the monolith structure body is surface treatable.

30. A method for adsorbing a sample comprising the steps of:
containing a monolith adsorbent in a container accommodating a liquid or a gaseous sample; and stifling the sample and the monolith adsorbent to adsorb a target component in the sample wherein the monolith adsorbent is constructed by containing an adsorbing material in a monolith structure body, wherein the adsorbing material is exposable on the surface of the structure body, and the structure body is surface treatable.

31. A method for adsorbing a sample comprising the steps of:
  containing a monolith adsorbent in a container accommodating a gaseous sample; and
  performing passive sampling wherein the monolith adsorbent is constructed by containing an adsorbing material in a monolith structure body, wherein the adsorbing material is exposable on the surface of the structure body, and the structure body is surface treatable.

32. A method for adsorbing a sample comprising the steps of:
  inserting a tube accommodating a monolith adsorbent into a gas phase part of a vial; and
  blowing an inert gas into the sample from outside of the vial through a vial cap to transfer a target component in the sample to the gas phase part of the vial and to allow the monolith adsorbent to retain the target component in the sample wherein the monolith adsorbent is constructed by containing an adsorbing material in a monolith structure body, wherein the adsorbing material is exposable on the surface of the monolith structure body, and the monolith structure body is surface treatable.

33. The method for adsorbing a sample of claim 32, wherein
  the inert gas is selected from the group consisting of a helium gas and sodium gas.

* * * * *